(12) United States Patent
Liu et al.

(10) Patent No.: US 11,147,697 B2
(45) Date of Patent: Oct. 19, 2021

(54) EXPANDING DEVICE

(71) Applicant: TONKIN LIU STENTS LIMITED, London (GB)

(72) Inventors: Anna Liu, London (GB); Michael Tonkin, London (GB)

(73) Assignee: TONKIN LIU STENTS LIMITED, London (GB)

( * ) Notice: Subject to any disclaimer, the term of this patent is extended or adjusted under 35 U.S.C. 154(b) by 216 days.

(21) Appl. No.: 16/472,842

(22) PCT Filed: Dec. 21, 2017

(86) PCT No.: PCT/GB2017/053852
§ 371 (c)(1),
(2) Date: Jun. 21, 2019

(87) PCT Pub. No.: WO2018/115881
PCT Pub. Date: Jun. 28, 2018

(65) Prior Publication Data
US 2019/0350731 A1    Nov. 21, 2019

(30) Foreign Application Priority Data
Dec. 23, 2016  (GB) .................................. 1622215

(51) Int. Cl.
*A61F 2/91*   (2013.01)
*A61F 2/844*  (2013.01)
*A61F 2/04*   (2013.01)

(52) U.S. Cl.
CPC ................ *A61F 2/91* (2013.01); *A61F 2/844* (2013.01); *A61F 2002/041* (2013.01);
(Continued)

(58) Field of Classification Search
CPC ...... A61F 2/91; A61F 2/844; A61F 2002/043; A61F 2002/044; A61F 2002/046; A61F 2230/0013
See application file for complete search history.

(56) References Cited

U.S. PATENT DOCUMENTS 8,187,315 B1    5/2012  Clauson et al.
2001/0012961 A1  8/2001  Deem et al.
(Continued)

FOREIGN PATENT DOCUMENTS

FR    2797176 A1    2/2001
SU    1635980 A1    3/1991
(Continued)

OTHER PUBLICATIONS

International Search Report and Written Opinion dated Mar. 7, 2018 in connection with corresponding International Application No. PCT/US2017/053852.

*Primary Examiner* — Brian A Dukert
(74) *Attorney, Agent, or Firm* — Stout, Uxa & Buyan, LLP; Donald E. Stout

(57) ABSTRACT

A self-expandable stent (1) formed of a flexible, part-tubular body (2), anchoring portions (3) extending from each end of the body (2) and an array (4) of holes or perforations (40, 41, 42) through the body (2) and anchoring portions (3). The body (2) includes an open side (20) and a pair of axial edges (21) extending along a longitudinal axis (L) of the stent (1). The body (2) also includes a central portion (5) and a pair of axial edge portions (6) joining the central portion (5) to the axial edges (21). The central portion (5) of the body (2) is invertible from a relaxed, part-tubular condition to a flexed, inverted part-tubular condition in which the axial edges (21) overlap or converge toward one another for insertion and
(Continued)

release in a lumen (TR, TET) to expand, bear against and support a wall of the lumen (TR, TET).

20 Claims, 12 Drawing Sheets

(52) U.S. Cl.
CPC ... *A61F 2002/043* (2013.01); *A61F 2002/044* (2013.01); *A61F 2002/045* (2013.01); *A61F 2002/046* (2013.01); *A61F 2210/0014* (2013.01); *A61F 2230/0013* (2013.01); *A61F 2250/0059* (2013.01)

(56) References Cited

U.S. PATENT DOCUMENTS

| | | |
|---|---|---|
| 2001/0053932 A1 | 12/2001 | Phelps et al. |
| 2002/0007222 A1 | 1/2002 | Desai |
| 2002/0042564 A1 | 4/2002 | Cooper et al. |
| 2002/0107540 A1 | 8/2002 | Whalen et al. |
| 2005/0096498 A1 | 5/2005 | Houser et al. |
| 2006/0037617 A1 | 2/2006 | Walke et al. |
| 2008/0039931 A1 | 2/2008 | Jelle et al. |
| 2009/0005860 A1 | 1/2009 | Gale et al. |
| 2009/0209972 A1 | 8/2009 | Loushin et al. |
| 2009/0270971 A1 | 10/2009 | Xiao et al. |
| 2009/0326640 A1 | 12/2009 | Yoshimura et al. |
| 2010/0262156 A1 | 10/2010 | Melder |
| 2011/0022149 A1 | 1/2011 | Cox et al. |
| 2011/0288625 A1 | 11/2011 | Morgan et al. |
| 2012/0035715 A1 | 2/2012 | Robida et al. |
| 2014/0072610 A1 | 3/2014 | Venkatraman et al. |
| 2014/0079758 A1 | 3/2014 | Hall et al. |
| 2015/0148886 A1 | 5/2015 | Rao et al. |
| 2015/0223922 A1 | 8/2015 | Allen et al. |
| 2015/0272750 A1 | 10/2015 | Roth |
| 2015/0342765 A1 | 12/2015 | Weiner et al. |
| 2016/0128852 A1 | 5/2016 | Leanna et al. |
| 2016/0193029 A1 | 7/2016 | Shalev |
| 2016/0199085 A1 | 7/2016 | Hong et al. |

FOREIGN PATENT DOCUMENTS

| | | |
|---|---|---|
| WO | 03099165 A1 | 12/2003 |
| WO | 2016030898 A1 | 3/2016 |

EXPANDING DEVICE

This invention relates generally to an expanding device, for example a self-expanding device or geometrically-expanding device, for insertion into a cavity or tubular member. More particularly, although not exclusively, this invention relates to a self-expanding or geometrically-expanding support device that is configured to bear against a surface or wall of a cavity or tubular member to provide support thereto. The present invention is particularly advantageous in medical applications, but it may be applied to non-medical applications without departing from the scope of the present disclosure.

Expandable devices for supporting the lumen of an anatomic vessel or duct are known. The human body includes various lumens, such as arteries, blood vessels, intestines, urinary, biliary, bronchi, nasal, oesophageal or renal tracts, a trachea and so on. Such lumens can weaken, become occluded or otherwise require support. These symptoms can be caused, for example, by tumors, the formation of plaque, aneurysms, renovascular hypertension, stricture of the bile ducts and constriction of the esophagus or airway.

Stents are well known for opening a blocked or partially blocked body lumens. For example, when used in a blood vessel the stent opens the occluded vessel to achieve improved blood flow. The use of stents is also increasing in popularity for supporting other body lumens, such as airways. Airway obstructions cause breathlessness and difficulty swallowing and can be debilitating. These symptoms often occur in patients with lung cancer and tracheomalacia (collapsed airway), those requiring palliative treatment and trauma victims.

One preferred treatment for airway obstruction is surgical resection and tissue-engineered trachea have recently proven to be extremely effective in transplant trials. However, transplanted tissue-engineered trachea can become flaccid, requiring the use of a tracheal stent. Placement of such a stent into the tissue-engineered trachea, either before the procedure or after, can be extremely challenging. This issue is particularly acute when using conventional stents, the reasons for which will be appreciated by those skilled in the art.

Stents that are available commercially for such other purposes are largely adapted from vascular stents and have not generally been optimized for such other applications.

US20150342765 describes one such device, namely an endoluminal stent adapted for placement in the trachea of a patient. The stent described in this document has an open framework formed of interconnected struts defining interstices therebetween. The stent can a concave cross-sectional shape with a radius of curvature that is larger than that of the trachea within which it is received to provide support thereto.

Whilst effective, the Applicant has observed that such devices could be improved. In particular, it would be beneficial to provide a flexible stent that would minimise irritation to the bodily lumen within which it is inserted, would not require regular replacement and which would allow for easy removal. There is also a growing need for a stent that is more adaptable to different uses. There is also a growing need for a more biocompatible and/or biostable stent.

Accordingly, a first aspect of the invention provides a self-expandable or geometrically-expandable device comprising a flexible, part-tubular body having an open side with a pair of axial edges extending therealong, wherein at least part of the body is invertible from a first and/or relaxed, part-tubular condition to a second and/or flexed and/or inverted part-tubular condition in which the axial edges overlap or converge toward one another, e.g. such that when inserted or implanted into a cavity or tubular member the device expands and bears against a wall thereof.

Whilst not wishing to be bound by any particular theory, the provision of a flexible, inverted part-tubular body is believed to enable the device to provide a substantially constant, or at least more consistent, expansion force to the wall of the cavity or tubular member across a wider range of sizes. Whilst not wishing to be bound by any particular theory, this is believed to be particularly advantageous for flaccid walls, such as those of a tissue-engineered trachea or any other tubular member or cavity, whether or not in the body of a human or animal.

The device may comprise a retaining means or element. The retaining means or element may be configured or operable to retain, in use, the body or at least part thereof in the second or flexed or inverted condition, e.g. prior to insertion into a cavity or tubular member.

The cavity or tubular member may comprise a lumen. The device may comprise a medical device, for example an implantable medical device. The device may comprise a stent, graft or other implantable device. The device may comprise a short-term or temporary implant. The device may be removable.

Another, more specific aspect of the invention provides a self-expandable or geometrically-expandable stent comprising a flexible, part-tubular body having an open side with a pair of axial edges extending therealong, at least part of the body being invertible from a relaxed, part-tubular condition to a flexed, inverted part-tubular condition in which the axial edges overlap or converge toward one another, wherein the body is retained, in use, in the flexed condition by a retaining means for insertion and release in a lumen to expand, bear against and support a wall of the lumen.

It will be appreciated that any of the features described herein may apply to any aspect of the invention, whether the device is used as a medical device or for any other application.

The body may comprise a central portion and/or one or more, e.g. a pair of, axial edge portions. The axial edge portions may join the central portion to the axial edges. The body may be configured such that a pressure exerted, in use, on the lumen wall by the axial edge portions is less than that which is exerted by at least part of the central portion.

Another aspect of the invention provides a self-expandable or geometrically-expandable device comprising a flexible, part-tubular body having an open side with a pair of axial edges extending therealong, the body comprising a central portion and a pair of axial edge portions joining the central portion to the axial edges, at least part of the body being invertible from a relaxed, part-tubular condition to a flexed, inverted part-tubular condition in which the axial edges overlap or converge toward one another for insertion and release in a lumen to expand, bear against and support a wall of the lumen, wherein the body is configured such that a pressure exerted, in use, on the lumen wall by the axial edge portions is less than that which is exerted by at least part of the central portion.

The or each axial edge portion may have a positive curvature when the body is in the relaxed condition and/or when the body is in the flexed condition. The central portion may have a negative curvature when the body is in the relaxed condition. The central portion may have a positive curvature when the body is in the flexed condition. The radius of curvature of the central portion may be similar or substantially the same as the radius of curvature of the axial edge portions when the body is in the flexed condition.

The device or body may have a first side and a second side, each of which may be a major side. The or each axial edge portion may be convex on the first side and/or concave on the second side, for example when the body is in the relaxed condition and/or when the body is in the flexed condition. The central portion may be concave on the first side, for example when the body is in the relaxed condition. The central portion may be convex on the second side, for example when the body is in the flexed condition.

The central portion may be invertible. In embodiments, the body part that is invertible or that is configured to be inverted may comprise or consist only of the central portion. In embodiments, the axial edge portions may not be invertible or may be configured to remain un-inverted.

By providing this counter inversion, wherein the axial edge portions curve in the opposite direction to the central portion, the outward or expanding pressure applied by the device when in the flexed condition may be reduced, for example to nil, toward, at or adjacent the axial edges. Moreover, the axial edges can be configured to avoid penetrating into or damaging the tubular member or cavity when the body is inverted and released therein.

At least one or each of the axial edge portions of the body may have a different thickness to the central portion of the body. The central portion may have a first thickness and/or at least one or each of the axial edge portions may have a second thickness. The second thickness is preferably less than the first thickness. Alternatively, the second thickness may be more than the first thickness.

The thickness of the body or central portion may vary, for example from a maximum thickness in a central region of the central portion to or toward the axial edge portions or vice versa. Additionally or alternatively, the thickness of the body or central portion may vary, for example along the axis of the device or body. The thickness may vary from a maximum thickness in a central region of the central portion to or toward one or each axial end of the device or body or vice versa. The thickness may vary from a maximum thickness from one axial end to another.

The thickness of at least one or each of the axial edge portions may vary, for example from a maximum thickness adjacent or at an interface with the central portion of the body to or toward the axial edge thereof or vice versa. Alternatively, the thickness of at least one or each of the axial edge portions may vary from a maximum thickness in a central region thereof to or toward the axial edge thereof or vice versa. Additionally or alternatively, the thickness of at least one or each of the axial edge portions may vary, for example along the axis of the device or body. The thickness may vary from a maximum thickness in a central region of the or each axial edge portion to or toward one or each axial end of the device or body or vice versa. The thickness may vary from a maximum thickness from one axial end of the axial edge portion to another. The thickness of at least one or each of the axial edge portions may vary in a similar or different manner to the central portion.

One or more anchoring portions may be provided, at least one of which may extend axially from an end of the body, for example when the body is in the relaxed condition and/or when the body is in the flexed condition. At least one of the anchoring portions may comprise a petal, flap, finger, barb or hook. One or more anchoring portions may extend axially from each end of the body, for example when the body is in the relaxed condition and/or when the body is in the flexed condition.

Another aspect of the invention provides a self-expandable or geometrically-expandable device comprising a flexible, part-tubular body having an open side with a pair of axial edges extending therealong and one or more anchoring portions extending axially from at least one end thereof, at least part of the body being invertible from a relaxed, part-tubular condition to a flexed, inverted part-tubular condition in which the axial edges overlap or converge toward one another, wherein the or each anchoring portion is configured such that when the body or body portion is inverted to the flexed condition the or each anchoring portion is biased toward extending axially and outwardly from the end of the body, thereby to bear against the wall of the lumen for inhibiting movement of the stent.

The thickness of at least one or each of the anchoring portions may vary, for example from a maximum thickness adjacent or at an interface with the central portion of the body to or toward an axial end thereof or vice versa. Alternatively, the thickness of at least one or each of the anchoring portions may vary from a maximum thickness in a central region thereof to or toward an axial end thereof or vice versa. Additionally or alternatively, the thickness of at least one or each of the anchoring portions may vary, for example along the axis of the device or body. The thickness may vary from a maximum thickness in a central region of the or each anchoring portion to or toward one or each axial end of the device or body or vice versa. The thickness may vary from a maximum thickness from one axial end of an anchoring portion at a first axial end of the device or body to an axial end of another anchoring portion at a second end of the device or body. The thickness of at least one or each of the anchoring portions may vary in a similar or different manner to the central portion and/or to the axial edge portion(s).

The device may be inverted symmetrically along its vertical axis. The geometry of the body, e.g. its cross section, may create an even or substantially even outward pressure along the body, for example up to the or each anchoring portion.

At least one or each anchoring portion may extend inwardly from the end of the body when the body is in the relaxed condition. At least one or each anchoring portion may extend outwardly from the end of the body when the body is in the relaxed condition, e.g. thereby to bear against the wall of the lumen. This configuration may be configured or suitable for inhibiting movement or migration thereof. Additionally or alternatively, this configuration may be configured or suitable for reducing the pressure exerted, in use, on the lumen wall by the axial edge portions.

For the avoidance of doubt, the terms "inward" and "outward" and related terms are used to describe directions relative to the part-tubular shape of the body.

The or each anchoring portion may include a positive curvature when the body is in the relaxed condition and/or when the body is in the flexed condition. The or each anchoring portion may include a central part. The central part may have a positive curvature when the body is in the relaxed condition and/or when the body is in the flexed condition. The or each anchoring portion may include one or more axial sides. The or each axial side may have a negative curvature when the body is in the relaxed condition.

At least one or each anchoring portion may be configured such that when the body or body portion is inverted to the flexed condition, the or each anchoring portion extends or is biased toward extending outwardly from the end of the body, e.g. thereby to bear against the wall of the lumen for inhibiting movement or migration thereof. The outward biasing of the or each anchoring portion may be due to or caused by the anchoring portion extending inwardly from the end of the body when the body is in the relaxed condition. Additionally or alternatively, the outward biasing of the or each anchoring portion may be due to or caused by the negative curvature of the axial side(s) of the anchoring portion when the body is in the relaxed condition. The or each axial side of the anchoring portion may have a positive curvature when the body is in the flexed condition.

The one or more anchoring portions comprise two or more anchoring portions. The one or more anchoring portions may comprise two or more anchoring portions extending from each end. The anchoring portions may be provided by a series of undulations or crests joined to the body at their root. The two or more anchoring portions extending from each end or from the same end may converge toward one another, for example when the body is in the relaxed condition. The two or more anchoring portions extending from each end or from the same end may diverge from one another, for example when the body is in the flexed condition.

The device may comprise a loading configuration, e.g. for inserting and/or loading the device into a tubular member or cavity. The anchoring portions extending from the or each end may be folded inwardly and/or may be held by the retaining means in an overlapping relationship to retain the body in its flexed condition in the loading configuration.

The device may comprise a deployed configuration, e.g. for bearing against and/or supporting a wall of a tubular member or cavity. The body may be in the flexed condition and/or may be expanded and/or may bear against a wall of a tubular member or cavity in the deployed configuration. The or each anchoring portion may be deployed and/or may extend outwardly from the end of the body and/or may bear against or be configured to bear against a wall of a tubular member or cavity in the deployed configuration.

The retaining means may be operable to change or release, in use, the device from the loading configuration and/or to expand to the deployed configuration, for example when the device is in a tubular member or cavity. The retaining means may be operable to release, in use, the body and/or the anchoring portions. The retaining means may be operable to release, in use, the anchoring portions such that the device changes or expands from the loading configuration and/or to the deployed configuration. The retaining means may be operable to release, in use, the anchoring portions to enable the anchoring portions and the body to expand to a deployed configuration, e.g. from the loading configuration.

At least one or each anchoring portion may include a retaining hole, e.g. through its thickness and/or adjacent a free end thereof. The retaining means may comprise a retainer.

The retaining means or retainer may comprise an elongate element or a release cord, which may be inserted or insertable into and/or extend through the hole. The retaining means or retainer may, but need not, comprise a stowing pin, which may be inserted or insertable into the retaining hole and/or engage the or each anchoring portion and/or which may be connected to or otherwise associated with the release cord. The stowing pin may be frangibly connected to the release cord.

Additionally or alternatively, the retaining means or retainer may comprise a cover or jacket, which may be tubular and/or within which the device is or may be received when in the flexed condition and/or when in the loading configuration. The cover or jacket may comprise a casing, bag or tube, for example a catheter. The cover or jacket may be retractable, in use, to release the device, e.g. to enable the device to expand, bear against and/or support a wall of the tubular member or cavity. The cover or jacket may be retractable, in use, to release the device from the loading configuration and/or to expand to the deployed configuration, for example when the device is in a tubular member or cavity.

The device may be removable. The device may comprise a removal configuration, for example a flexed condition in which it is contracted or constricted relative to the deployed configuration and/or in which the longitudinal sides are retracted relative to the deployed configuration. The device may be reconfigurable into the removal configuration by a removal device or tool. The retaining means, for example the cover or jacket, may be comprised in a surgical device, such as a catheter or scope. The surgical device may comprise a removal tool for contracting or constricting the device from the deployed configuration and/or for reconfiguring the device form the deployed configuration to the removal configuration.

At least part of the body may comprise projections and/or recesses or depressions and/or undulations. At least part of the body may undulate, for example to provide a series of ridges and/or valleys, which may be for engaging the wall and/or for describing together with the wall a series or array or network of channels.

Another aspect of the invention provides a self-expandable or geometrically-expandable device comprising a flexible, part-tubular undulating body having an open side with a pair of axial edges extending therealong, wherein at least part of the body is invertible from a relaxed, part-tubular condition to a flexed, inverted part-tubular condition in which the axial edges overlap or converge toward one another for insertion and release in a lumen to expand, bear against and support a wall of the lumen such that a series of ridges and valleys formed by the undulating body engage the lumen wall and/or describe together with the wall a series or array or network of channels.

At least part of the body may undulate along an axial direction or dimension and/or along a circumferential direction or dimension thereof. At least part of the body may comprise a thickness through which the undulations may be formed. At least part of the body may comprise projections on one side with corresponding recesses or depressions on the opposite side, for example arranged in an array, e.g. a grid or diagrid. At least part of the body may comprise both projections and depressions on each side, e.g. each major side thereof. Each undulation may comprise recesses or depressions or valleys on one side and corresponding projections or ridges on the opposite side.

The thickness of the body may comprise a base thickness or gauge. The body may have an effective thickness, for example resulting from the undulations. The effective thickness may be described between the peaks of the undulations, projections or ridges on each side of the body or comprise or correspond to the distance therebetween. The effective thickness may be described between the peaks of the undulations, projections or ridges on one side of the body and the peaks of the undulations, projections or ridges on the other side of the body or comprise or correspond to the distance therebetween. The effective thickness may comprise the amplitude of the undulating body, which may be described between the peaks of the undulations, projections or ridges on one side of the body and the peaks of the undulations, projections or ridges on the other side of the body.

The skilled person will appreciate that the undulations provide a greater resistance to bending along a direction perpendicular to the undulations. For example, undulations along the circumferential direction increase the body's resistance to bending in the axial direction. Similarly, undulations along the axial direction increase the body's resistance to bending in the circumferential direction, which increases the expansion force of the body in the inverted condition. The skilled person would also appreciate that the body's resistance to bending is increased in both the axial and circumferential directions when undulations are provided in both the circumferential and axial directions.

The ratio of effective thickness to base thickness or gauge is indicative of the extent of such increase in resistance. This ratio may be selected to suit the specific application.

The axial edges of the body may undulate, for example in a direction perpendicular to the thickness of the body. The axial edges of the body may undulate to provide a series of smooth and/or curved projections or crests, e.g. for engaging the wall or a tubular member or cavity without penetrating it. When the device comprises a stent for implantation into a lumen which includes a series of muscular or cartilage rings, the undulations of the axial edges may be configured, e.g. sized and/or dimensioned, to engage such rings, for example such that the projections or crests are received or lodged between such rings.

The body may comprises an array of perforations, apertures or holes (hereinafter holes) through its thickness.

Another aspect of the invention provides a self-expandable or geometrically-expandable device comprising a flexible, part-tubular body having an array of holes through its thickness and an open side with a pair of axial edges extending therealong, wherein at least part of the body is invertible from a relaxed, part-tubular condition to a flexed, inverted part-tubular condition in which the axial edges overlap or converge toward one another for insertion and release in a lumen to expand, bear against and support a wall of the lumen.

The or each hole may be free of sharp edges and/or may comprise a closed curve. The array may comprise a grid, for example a diagrid. At least one of the anchoring portions may comprise one or more of the holes. The array of holes may extend into at least one or each anchoring portion. At least one of the holes in the or each anchoring portion may be smaller than at least one or each or all of the holes in the body.

It will be appreciated by the skilled person that the density and size of holes will affect the rigidity or resistance to bending of the device or body. The device or body or central portion or edge portions or anchoring portions may each have a hole coverage and/or hole density. The hole coverage may comprise the proportion of the aggregate hole area compared with the area of the device or body or central portion or edge portion or anchoring portion.

The hole coverage of the edge portions of the body is preferably less than that of the central portion. Similarly, the hole coverage of the anchoring portions of the body may be less than that of the central portion and/or more than that of the edge portions.

The lumen may comprise any passageway or cavity in a living organism (e.g., bile duct, bronchiole tubes, nasal cavity, blood vessels, heart, oesophagus, trachea, stomach, fallopian tube, uterus, ureter, urethra, the intestines, lymphatic vessels, nasal passageways, eustachian tube, acoustic meatus, etc.). Alternatively, the tubular member or cavity may comprise a pipe, tube, membrane or any other tubular member or cavity, which may be formed of any suitable material, e.g. requiring support.

The device may comprise a medicament coated on the body and/or loaded into at least one of the holes or coated on an internal surface of at least one of the holes.

The stent may comprise a tracheal stent or a vascular stent or an oesophageal stent or a bronchial stent or a biliary stent or a nasal stent or an intestinal stent or a urinary stent. The device may comprise a non-tracheal stent, meaning any stent that is not configured for use in a trachea.

The device or stent may be formed of any suitable material that is capable of functioning in the manner described. The device or stent may, in particular, be formed at least in part of or include one or more portions, parts, segments or sections formed at least in part of engineered cartilage. Additionally or alternatively, the device or stent may be formed at least in part of or include one or more portions, parts, segments or sections formed at least in part of a plastics or polymeric material, preferably one which is biostable or at least substantially biostable, particularly when the device or stent is for medical applications. In embodiments, the device or stent may be formed at least in part of or include one or more portions, parts, segments or sections formed at least in part of a composite material including engineered cartilage and a biostable polymeric material. The biostable polymeric material may comprise any suitable material including, but not limited to, those described below in relation to the specific embodiments. In embodiments, one or more parts of the device or stent, e.g. the body and anchoring portions, are formed integrally.

Another, more specific aspect of the invention provides a self-expandable or geometrically-expandable device comprising a flexible, part-tubular undulating body having an array of holes through its thickness and an open side with a pair of axial edges extending therealong, at least part of the body being invertible from a relaxed, part-tubular condition to a flexed, inverted part-tubular condition in which the axial edges overlap or converge toward one another for insertion and release in a lumen to expand, bear against and support a wall of the lumen such that a series of ridges and valleys formed by the undulating body engage the lumen wall, the body comprising a central portion, a pair of axial edge portions joining the central portion to the axial edges and one or more anchoring portions extending axially from at least one end of the body, wherein each axial edge portion has a positive curvature both when the body is in the relaxed condition and when the body is in the flexed condition, the central portion has a negative curvature when the body is in the relaxed condition and a positive curvature when the body is in the flexed condition and the or each anchoring portion is biased, when the body or body portion is inverted to the flexed condition, toward extending axially and outwardly from the end of the body, thereby to bear against the wall of the lumen for inhibiting movement of the stent.

Another aspect of the invention provides a tissue-engineered lumen, ex vivo, within which is received a device as described above.

Another aspect of the invention provides a kit of parts comprising a self-expandable or geometrically-expandable device as described above and a retaining means for retaining, in use, the body in the flexed condition for insertion and release in a tubular member or cavity.

The kit may form part of a surgical kit or system.

Another aspect of the invention provides a surgical kit comprising a surgical device and a self-expandable or geometrically-expandable device as described above. The surgical device may comprise a scope. The surgical device may comprise a tubular member, such as cover or jacket, for example a cover or jacket as described above.

The surgical device may comprise a pushing means or pusher, e.g. for releasing and/or pushing the self-expandable or geometrically-expandable device out of the tubular member. The pushing means or pusher may be received within the tubular member. Additionally or alternatively, the tubular member may be retractable, e.g. relative to the pusher and/or for releasing the self-expandable or geometrically-expandable device. The pushing means or pusher may be operable, and/or the tubular member may be retractable, to enable the self-expandable or geometrically-expandable device to expand, bear against and/or support a wall of the tubular member or cavity.

The surgical device may be operable to contract or constrict the self-expandable or geometrically-expandable device from its deployed configuration. The surgical device may be operable to retract the self-expandable or geometrically-expandable device into the tubular member, for example in the contracted or constricted condition. The surgical device may comprise a gripping tool, which may be receivable within the tubular member and/or which may be operable to effect the contraction or constriction and/or retraction. In some embodiments, the gripping tool may comprise a pair of hooks for engaging one of the holes in the self-expandable or geometrically-expandable device. The gripping tool may be operable to draw the hooks toward one another, for example to contract or constrict the self-expandable or geometrically-expandable device. The gripping tool may be operable to retract the hooks into the tubular member, for example to reconfigure the self-expandable or geometrically-expandable device from its deployed configuration, e.g. to or toward its removal configuration.

In other embodiments, the gripping tool may comprise a pair of jaws, e.g. forceps, which may be operable to grab or grip part of the self-expandable or geometrically-expandable device. The gripping tool may be operable to rotate and/or retract the jaws, e.g. relative to the tubular member. The gripping tool may be operable to cause the jaws to grab or grip and rotate part of the self-expandable or geometrically-expandable device, for example to reconfigure it from its deployed configuration to or toward its removal configuration. The gripping tool may be further operable to cause the jaws to retract, e.g. relative to the tubular member, to remove, in use, the self-expandable or geometrically-expandable device, e.g. from a lumen. The gripping tool may be operable to cause the jaws to grab or grip and rotate part of the self-expandable or geometrically-expandable device and retract, e.g. relative to the tubular member, to remove, in use, the self-expandable or geometrically-expandable device.

Another aspect of the invention provides a method of preparing and/or using and/or implanting an expandable device, e.g. as described above. The method may comprise the use of the kit parts or surgical kit described above.

The method may comprise preparing the device for implantation or insertion into a cavity or tubular member. The method may comprise inverting at least part of the body from the first and/or relaxed, part-tubular condition to the second and/or flexed and/or inverted part-tubular condition. The method may comprise constraining or retaining the device or body or body part in the second and/or flexed and/or inverted condition, for example using the retaining means.

Another aspect of the invention provides a method of preparing a device, e.g. a self-expanding or geometrically-expandable device for implantation or insertion into a cavity or tubular member, the method comprising inverting a flexible, part-tubular body of the stent from a relaxed, part-tubular condition to a flexed, inverted part-tubular condition, in which axial edges extending along an open side of the body overlap or converge toward one another, and retaining the body in the flexed, inverted condition ready for insertion and release in a lumen to expand, bear against and support a wall of the lumen.

The method may comprise configuring the device into the loading configuration. The method may comprise folding the anchoring portions, e.g. inwardly, and/or holding the anchoring portions, e.g. using the retaining means, in an overlapping relationship, for example to retain the body in its flexed condition.

The method may comprise inserting a release cord through a hole in the anchor portions, for example to retain the stent in the loading configuration. The method may comprise inserting a stowing pin into the hole in the anchor portions, for example such that the stowing pin engages each anchoring portion. The stowing pin may be associated with the release cord, for example operatively or physically or mechanically connected to the release cord. The stowing pin may be frangibly connected to the release cord.

The method may comprise inserting the device into a cover or jacket, which may be tubular and/or within which the device is or may be received when in the flexed condition and/or when in the loading configuration. The method may comprise inserting the device into a tubular member of a surgical device, for example in the flexed condition and/or loading configuration.

Another aspect of the invention provides a method of implanting a device, e.g. a self-expanding or geometrically-expandable device. The method may comprise one or more steps of the aforementioned method of preparing a device.

The method may comprise inserting the device into a tubular member or cavity, which may be a lumen. The method may comprise deploying the device and/or releasing the device in a tubular member or cavity, which may be a lumen. The method may comprise releasing the stent in the cavity or tubular member such that it expands, bears against and supports a wall of the cavity or tubular member. The method may comprise releasing or disengaging the retaining means from the device, for example by pulling the release cord.

The method may comprise inserting the device into a lumen or lumen segment in vitro or ex vivo, which lumen or lumen segment may comprise a natural or tissue engineered lumen, for example a trachea or trachea section or any other lumen. The method may comprise a resection procedure. The method may comprise inserting the device in vivo.

Another aspect of the invention provides a computer program element comprising and/or describing and/or defining a three-dimensional design for use with a simulation means or a three-dimensional additive or subtractive manufacturing means or device, e.g. a three-dimensional printer, CNC machine or injection moulding machine, the three-dimensional design comprising an embodiment of the self-expanding or geometrically-expanding device described above.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. For the avoidance of doubt, the terms "may", "and/or", "e.g.", "for example" and any similar term as used herein should be interpreted as non-limiting such that any feature so-described need not be present. Indeed, any combination of optional features is expressly envisaged without departing from the scope of the invention, whether or not these are expressly claimed. The applicant reserves the right to change any originally filed claim or file any new claim accordingly, including the right to amend any originally filed claim to depend from and/or incorporate any feature of any other claim although not originally claimed in that manner.

Embodiments of the invention will now be described by way of example only with reference to the accompanying drawings in which.

Figure 1:
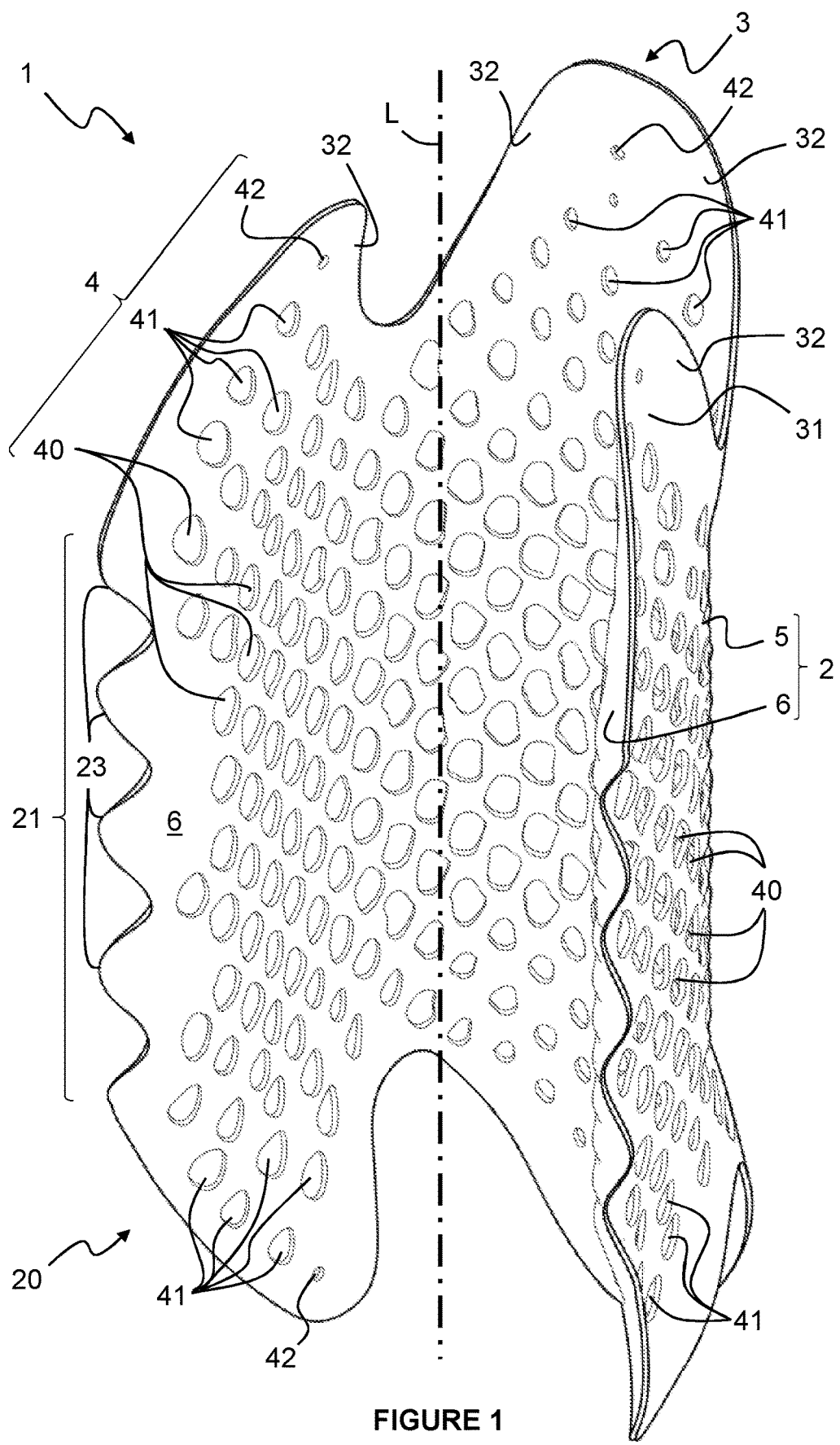
FIG. 1 is a perspective view of a self-expanding device according to an embodiment of the invention shown in a relaxed condition.
Figure 2:
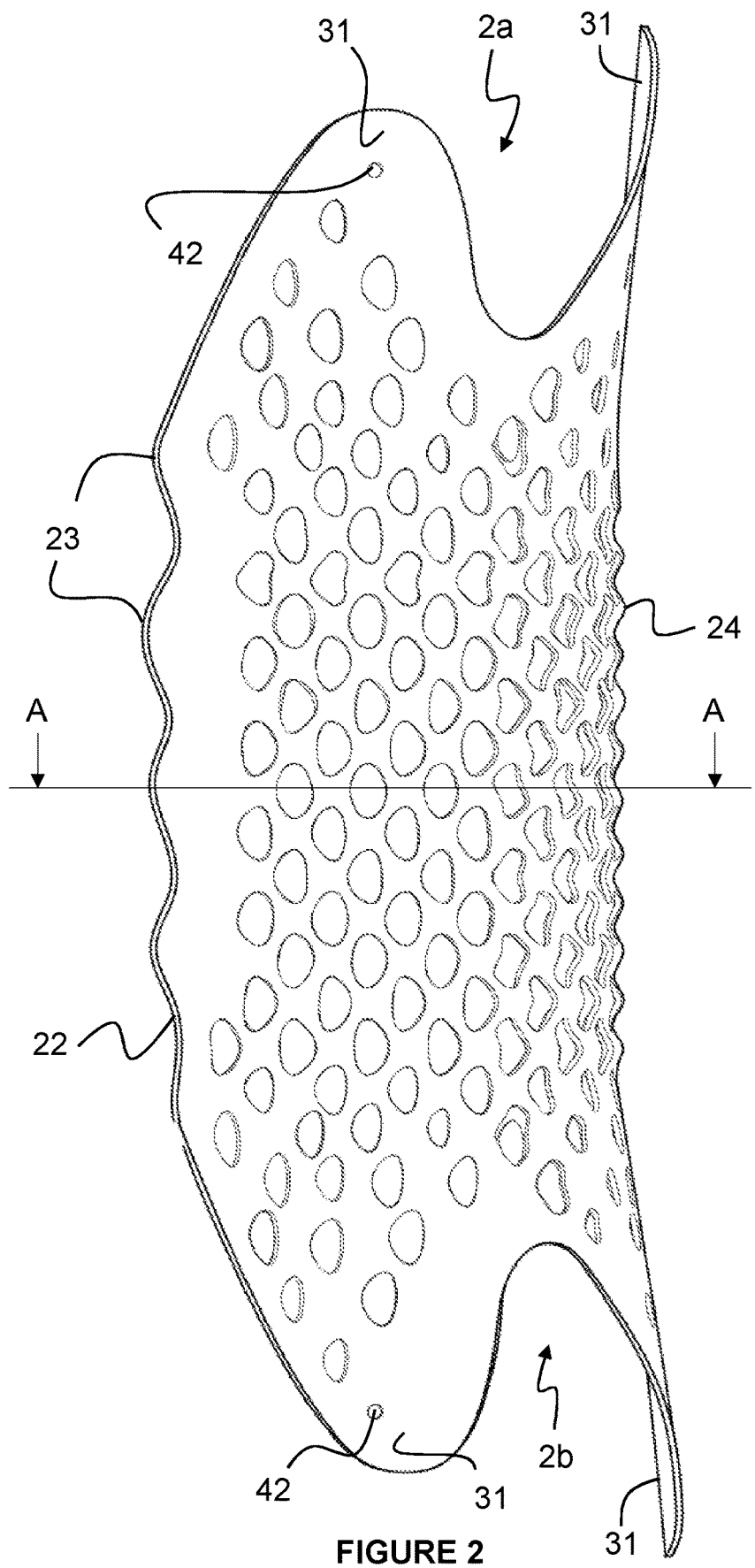
FIG. 2 is a side view of the device of FIG. 1.
Figure 3:
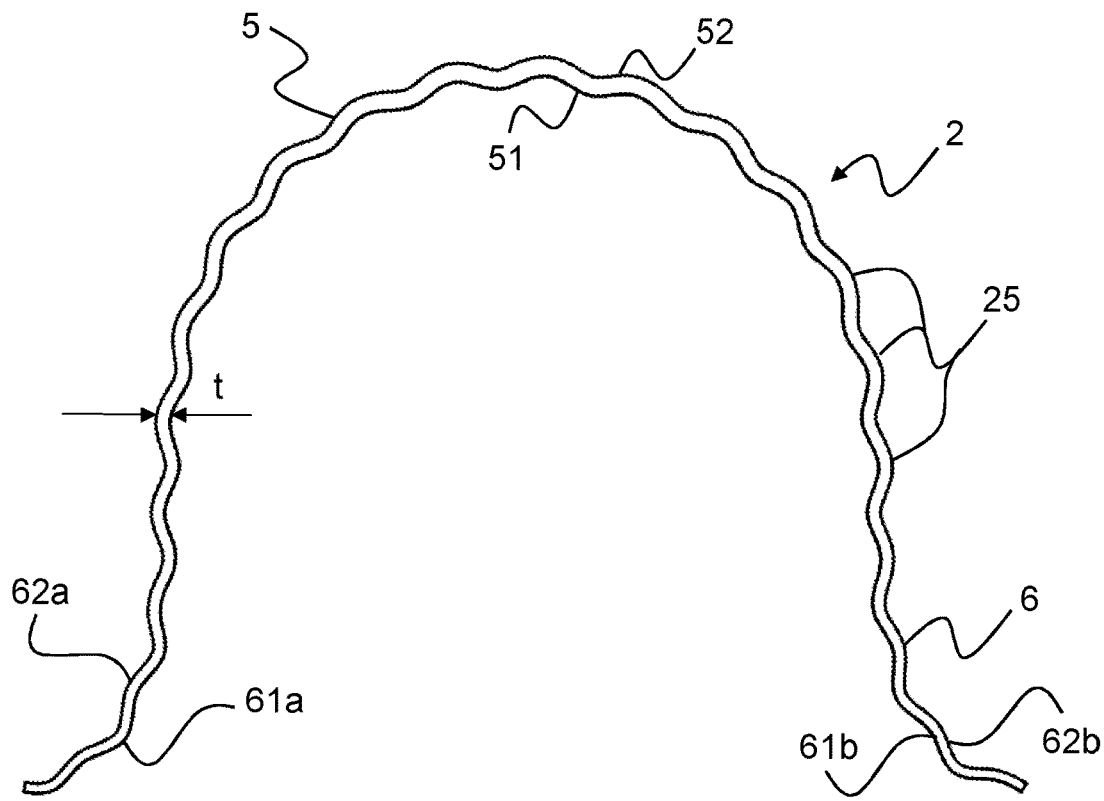
FIG. 3 is a section view through line A-A of FIG. 2.

Referring now to FIGS. 1 to 3, there is shown a self-expanding device 1, which is in the form of a tracheal stent 1 in this embodiment, shown in a relaxed condition. The stent 1 has a longitudinal axis L and includes a flexible, part-tubular body 2, six anchoring portions 3 and an array 4 of holes or perforations 40, 41, 42 through the body 2 and anchoring portions 3. The body 2 includes an open side 20 and a pair of axial edges 21 extending along the longitudinal axis L. The body 2 also includes a central portion 5 and a pair of axial edge portions 6 joining the central portion 5 to the axial edges 21.

In this embodiment, the body 2 and anchoring portions 3 are both formed integrally of a composite material including engineered cartilage and a biostable polymeric material. It is also envisaged that the body 2 may be formed solely of engineered cartilage or a biostable polymeric material.

Non-limiting examples of polymers that are considered to be biostable include, but are not limited to, parylene; parylene c; parylene f; parylene n; parylene derivatives; maleic anyhydride polymers; phosphorylcholine; poly n-butyl methacrylate (PBMA); polyethylene-co-vinyl acetate (PEVA); PBMA/PEVA blend or copolymer; polytetrafluoroethene and derivatives; poly-paraphenylene terephthalamide; poly(ether ether ketone) (PEEK); poly(styrene-b-isobutylene-b-styrene); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN; acrylic polymers and copolymers; glycosaminoglycans; alkyd resins; elastin; polyether sulfones; epoxy resin; poly(oxymethylene); polyolefins; polymers of silicone; polymers of methane; polyisobutylene; ethylene-alphaolefin copolymers; polyethylene; polyacrylonitrile; fluorosilicones; poly(propylene oxide); polyvinyl aromatics (e.g., polystyrene); poly(vinyl ethers) (e.g., polyvinyl methyl ether); poly(vinyl ketones); poly(vinylidene halides); poly(vinylpyrolidone); poly(vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer); vinyl halide polymers and/or copolymers; polyacrylic acid; ethylene acrylic acid copolymer; ethylene vinyl acetate copolymer; polyvinyl alcohol; poly(hydroxyl alkylmethacrylate); polyvinyl esters; and/or copolymers, blends, and/or composites thereof.

The body 2 and/or anchoring portions 3 may be coated with one or more biological agents. Advantageously, one or more of the body perforations 40 and/or anchoring portion perforations 41 may be coated or filled with one or more biological agents.

The term "biological agent" includes, but is not limited to, a substance or medicament formulated and/or designed to prevent, inhibit and/or treat one or more biological problems, and/or to promote the healing in a treated area. The following categories are envisaged: thrombolytics, vasodilators, anti-hypertensive agents, anti-microbial or anti-biotic, anti-mitotic, anti-proliferative, anti-secretory agents, non-steroidal anti-inflammatory drugs, immunosuppressive agents, growth factors and growth factor antagonists, chemotherapeutic agents, anti-polymerases, anti-viral agents, anti-body targeted therapy agents, hormones, anti-oxidants, radio-therapeutic agents, radiopaque agents and/or radio-labeled agents. Non-limiting examples of biological agents that can be used include, but are not limited to, 5-Fluorouracil and/or derivatives; 5-Phenylmethimazole and/or derivatives; ACE inhibitors and/or derivatives thereof; acenocoumarol and/or derivatives thereof; acyclovir and/or derivatives; actilyse and/or derivatives; adrenocorticotropic hormone and/or derivatives; adriamycin and/or derivatives; agents that modulate intracellular Ca2+ transport such as L-type (e.g., diltiazem, nifedipine, verapamil, etc.) or T-type Ca2+ channel blockers (e.g., amiloride, etc.); alpha-adrenergic blocking agents and/or derivatives; alteplase and/or derivatives; amino glycosides and/or derivatives; angiopeptin and/or derivatives; angiostatic steroid and/or derivatives; angiotensin II receptor antagonists and/or derivatives; anistreplase and/or derivatives; antagonists of vascular epithelial growth factor and/or derivatives; anti-biotics; anti-coagulant compounds and/or derivatives; anti-fibrosis compounds and/or derivatives; anti-fungal compounds and/or derivatives; anti-inflammatory compounds and/or derivatives; anti-invasive factor and/or derivatives; anti-metabolite compounds and/or derivatives; anti-matrix compounds and/or derivatives; anti-microbial agents and/or derivatives; anti-migratory agents and/or derivatives; anti-mitotic compounds and/or derivatives; anti-neoplastic compounds and/or derivatives; anti-oxidants and/or derivatives; anti-platelet compounds and/or derivatives; anti-proliferative compounds and/or derivatives; anti-thrombogenic agents and/or derivatives; argatroban and/or derivatives; ap-1 inhibitors and/or derivatives; aspirin and/or derivatives; azathioprine and/or derivatives thereof; β-Estradiol and/or derivatives; β-1-anticollagenase and/or derivatives; calcium channel blockers and/or derivatives thereof; calmodulin antagonists and/or derivatives; CAPTOPRIL and/or derivatives; cartilage-derived inhibitor and/or derivatives; ChIMP-3 and/or derivatives; cephalosporin and/or derivatives; chloroquine and/or derivatives; chemotherapeutic compounds and/or derivatives; chymostatin and/or derivatives clopidigrel and/or derivatives; clotrimazole and/or derivatives thereof; colchicine and/or derivatives; cortisone and/or derivatives; coumadin and/or derivatives; curacin-A and/or derivatives; cyclosporine and/or derivatives; cytochalasin and/or derivatives; cytokines and/or derivatives; desirudin and/or derivatives; dexamethazone and/or derivatives; dipyridamole and/or derivatives; eminase and/or derivatives; endothelin and/or derivatives; endothelial growth factor and/or derivatives; epidermal growth factor and/or derivatives; epothilone and/or derivatives; estramustine and/or derivatives; estrogen and/or derivatives; fenoprofen and/or derivatives; fluorouracil and/or derivatives; flucytosine and/or derivatives; forskolin and/or derivatives; ganciclovir and/or derivatives; glucocorticoids and/or derivatives; glycoprotein IIb/IIIa platelet membrane receptor antibody and/or derivatives; GM-CSF and/or derivatives; griseofulvin and/or derivatives; growth factors and/or derivatives; growth hormone and/or derivatives; heparin and/or derivatives; hirudin and/or derivatives; hyaluronate and/or derivatives; hydrocortisone and/or derivatives; ibuprofen and/or derivatives; immunosuppressive agents and/or derivatives; indomethacin and/or derivatives; inhibitors of the sodium/calcium antiporter and/or derivatives; inhibitors of the IP3 receptor and/or derivatives; inhibitors of the sodium/hydrogen antiporter and/or derivatives; insulin and/or derivatives; interferon alpha-2-macroglobulin and/or derivatives; ketoconazole and/or derivatives; Lepirudin and/or derivatives; lisinipril and/or derivatives; lovastatin and/or derivatives; marevan and/or derivatives; mefloquine and/or derivatives; metalloproteinase inhibitors and/or derivatives; methotrexate and/or derivatives; metronidazole and/or derivatives; miconazole and/or derivatives; monoclonal antibodies and/or derivatives; mutamycin and/or derivatives; naproxen and/or derivatives; nitric oxide and/or derivatives; nitroprusside and/or derivatives; nucleic acid analogues and/or derivatives; nystatin and/or derivatives; oligonucleotides and/or derivatives; paclitaxel and/or derivatives; penicillin and/or derivatives; pentamidine isethionate and/or derivatives; phenindione and/or derivatives; phenylbutazone and/or derivatives; phosphodiesterase inhibitors and/or derivatives; plasminogen activator inhibitor-1 and/or derivatives; plasminogen activator inhibitor-2 and/or derivatives; platelet factor 4 and/or derivatives; platelet derived growth factor and/or derivatives; plavix and/or derivatives; prednisone and/or derivatives; prednisolone and/or derivatives; probucol and/or derivatives; progesterone and/or derivatives; prostacyclin and/or derivatives; prostaglandin inhibitors and/or derivatives; protamine and/or derivatives; protease and/or derivatives; protein kinase inhibitors and/or derivatives; quinine and/or derivatives; radioactive agents and/or derivatives; rapamycin and/or derivatives; receptor antagonists for histamine and/or derivatives; refludan and/or derivatives; retinoic acids and/or derivatives; revasc and/or derivatives; rifamycin and/or derivatives; sense or anti-sense oligonucleotides and/or derivatives; seramin and/or derivatives; steroids; seramin and/or derivatives; serotonin and/or derivatives; serotonin blockers and/or derivatives; streptokinase and/or derivatives; sulfasalazine and/or derivatives; sulfonamides and/or derivatives; sulphated chitin derivatives; sulphated polysaccharide peptidoglycan complex and/or derivatives; TH1 and/or derivatives; thioprotese inhibitors and/or derivatives; taxol and/or derivatives; ticlid and/or derivatives; ticlopidine and/or derivatives thereof; tick anti-coagulant peptide and/or derivatives; thioprotese inhibitors and/or derivatives; thyroid hormone and/or derivatives; tissue inhibitor of metalloproteinase-1 and/or derivatives; tissue inhibitor of metalloproteinase-2 and/or derivatives; tissue plasma activators; TNF and/or derivatives, tocopherol and/or derivatives; toxins and/or derivatives; tranilast and/or derivatives; transforming growth factors alpha and beta and/or derivatives; trapidil and/or derivatives; triazolopyrimidine and/or derivatives; vapiprost and/or derivatives; vinblastine and/or derivatives; vincristine and/or derivatives; zidovudine and/or derivatives. The one or more biological agents can be coated on and/or impregnated in the one or more holes 40, 41 or the surface of the body 2 or anchoring portions 3 surface features thereof by any appropriate mechanisms such as, but not limited to, spraying (e.g., atomizing spray techniques, etc.), dip coating, roll coating, sonication, brushing, plasma deposition, depositing by vapor deposition.

The axial edges 21 of the body 2 each include cartilage mapping undulations 22 which define a series of smooth projections or crests 23 which engage the cartilage rings of a trachea within which the stent 1 is to be received. The projections 23 are received between such rings to increase the grip and prevent the stent 1 moving once in place and deployed.

The body 2 also undulates through its thickness both along its axial dimension, creating axial undulations 24, and along its circumferential dimension, creating circumferential undulations 25. The combination of axial undulations 24 and circumferential undulations 25 provides a series of ridges and valleys for engaging the wall of the lumen to provide additional grip and a network of channels between the stent 1 and trachea wall to increase air ventilation and/or allow mucociliarly clearance. The curvature of the undulations 24, 25 of the present embodiment is selected to provide a diagrid of projections and depressions, which has the additional benefit of rigidifying the body 2 thereby to maintain more effectively tension between the stent 1 and the trachea wall.

In some embodiments, the cartilage mapping undulations 22 are sized/dimensioned to suit an individual patients' trachea to optimise the level of grip and comfort. It is envisaged that where the device is used in other lumena, for example where ventilation and/or grip is not required, then at least one of the undulations 22, 24 or 25 may be omitted. Additionally or alternatively, the scale and/or depth of curvature of the undulations 22, 24 and/or 25 may be increased or decreased depending on the application of the device. If the body 2 is sized such that there is no opening 20 when deployed within a trachea, complementary edge projections 23 may be configured to allow the axial edges 21 to mesh, thereby preventing relative movement of the axial edge portions 6 and twisting of the device 1.

Three anchoring portions 3 extend axially from each end 2*a*, 2*b* of the body 2 and include a segmented collar or petal-like structure, each having a central part 31 and axial sides 32. The anchoring portions 3 are extensions of the body 2 and have a thickness similar to that of the body 2. The petal-like structure of the anchoring portions 3 provides a deployable geometry, which also enables the anchoring portions 3 to be folded into a loading configuration, described below. Establishing a loading configuration facilitates insertion of the stent 1 into a lumen. The anchoring portions 3 are resilient such that when folded, in the absence of retaining means, they are biased to return toward their initial condition.

In the present embodiment, the anchoring portions 3 are located at and extend from both ends 2*a*, 2*b* of the body 2 such that when the stent 1 is deployed within a trachea, the grip provided by the anchoring portions 3 is to the healthy trachea area outside of the section being replaced. Other arrangements are envisaged, for example the anchoring portions 3 may have a finger like structure, may include one or more projections, undulations or crests attached to the ends 2*a*, 2*b* of the body 2 at their root or be of any other suitable shape and may extend from only one of a first end 2*a* or a second end 2*b* thereof.

In this embodiment, the body 2 also includes an array 4 of holes or perforations 40, 41, 42 that extending through the body 2 and anchoring portions 3. The holes 40, 41, 42 are in the form of a closed curve, substantially round in this embodiment, and free of sharp edges to prevent damage or irritation of the trachea. The array 4 is in the form of a grid structure, in particular a diagrid structure in this embodiment. The array 4 extends from the body 2 into each anchoring portion 3, with the size of the body perforations 40 being larger than the anchoring portion perforations 41. Each anchoring portion 3 also includes a retaining hole 42 through its thickness and adjacent its free end for receiving a retaining means for retaining the stent 1 in a flexed condition prior to deployment.

In some embodiments any of the holes 40, 41, 42 may have sharp edges. In others any or all of the holes 40, 41 may be absent. The holes 40, 41 may be of equal size and may be in a random arrangement or any suitable structural arrangement. Some or all of the holes 40, 41 may be replaced with depressions or recesses not extending entirely through the body 2, for example to provide a cavity designed to carry a biological agent, although through holes 40, 41 are preferred as they promote air circulation to and from the lumen. The spacing and/or size of the holes 40, 41 of the array 4 may be selected to create a body 2 with a defined structural strength. The array 4 may be confined to the body 2 or pass through at least one anchoring portion 3. The retaining hole 42 may be absent depending on the retention mechanism used or may be present on only some of the anchoring portions 3 and not others.

The cross sectional profile illustrated in FIG. 3 shows that the central portion 5 has a negative curvature while the axial edge portions 6 have a positive curvature. The central portion 5 has a first, inner major central surface 51 and a second, outer major central surface 52. Similarly, the axial edge portions 6 each have a first, inner major edge surface 61*a*, 61*b*, which are extensions of and are contiguous with the first inner major central surface 51, and second, outer major edge surface 62*a*, 62*b*, which are also extensions of and are contiguous with the second outer major central surface 52. In the present embodiment, with the body 2 in a relaxed condition the first major central surface 51 is generally concave, while the second major central surface 52 is generally convex. Further, in the relaxed condition the first major edge surfaces 61*a*, 61*b* are convex, while the second major edge surfaces 62*a*, 62*b* are concave.

It is envisaged that the amount of positive curvature of the axial edge portions 6 in the relaxed condition may vary depending on the amount of tension the device is required to produce when deployed. It is also envisaged that where the device is used in other bodily lumena, where is it advantageous or at least not disadvantageous to have the axial edge portions 6 penetrate into the said bodily lumen, at least one of the axial edge portions 6 may be straight in the relaxed condition. Alternatively, the axial edge portions 6 may have negative curvature or any combination of straight, negative curvature and positive curvature depending on the application.

In the present embodiment, the thickness 't' of the body 2 is at its greatest in the central portion 5 and gradually decreases towards the axial edges 21. This is advantageous as it provides the body 2 with greater rigidity in the central portion 5 than in the axial edge portions 6. It is envisaged, however, that the thickness T may increase from the central portion 5 towards at least one axial edge 21, decrease from the central portion 5 towards at least one axial edge 21, be uniform between the axial edges 21 or any combination of the above.

When the stent 1 is in the relaxed condition, the central part 31 of the anchoring portion 3 has a positive curvature and the anchoring portions 3 converge towards each other, that is to say each anchoring portion 3 extends slightly inwardly (as well as axially) from the end 2*a*, 2*b* of the body 2. In addition, the axial sides 32 of each anchoring portion 3 have a negative curvature, opposite the positive curvature of the central part 31, that is to say the axial sides 32 have a reversed curvature relative to the central part 31 of the anchoring portion 3.

Figure 4:
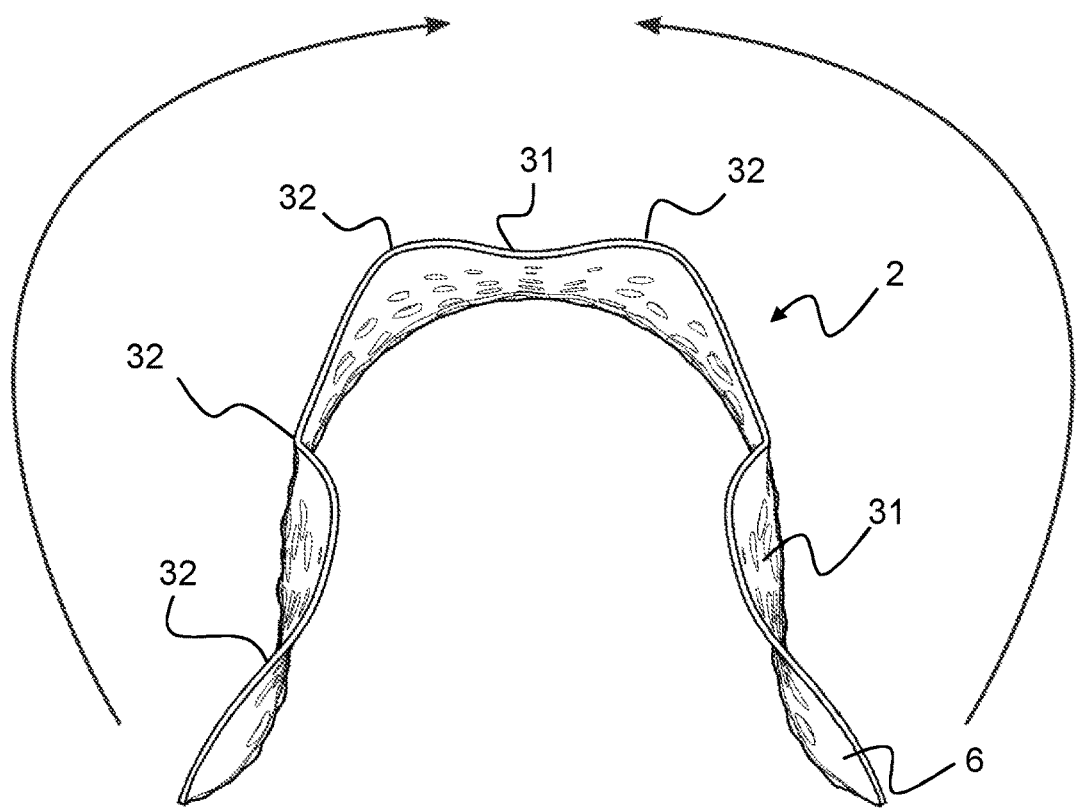
FIG. 4 is a top view of the device of FIGS. 1 to 3 illustrating the inversion direction.

In accordance with the invention and as illustrated more clearly in FIG. 4, the central portion 5 with a negative curvature is invertible from a relaxed condition to a flexed condition. This is achieved by urging the edge portions 6 relative to the central portion 5 in the direction indicated by the arrows until the body 2 inverts, or folds back on itself, into a flexed condition in which the central portion 5 has positive curvature. In the present embodiment the central portion 5 is invertible while the edge portions 6 remain in an un-inverted state. The inversion of the central portion 5 of the body 2 is necessary for the stent 1 to achieve a flexed condition, although it is envisaged that the axial edge portions 6 may also be invertible such that they are inverted when the device is in the flexed condition.

Figure 5:
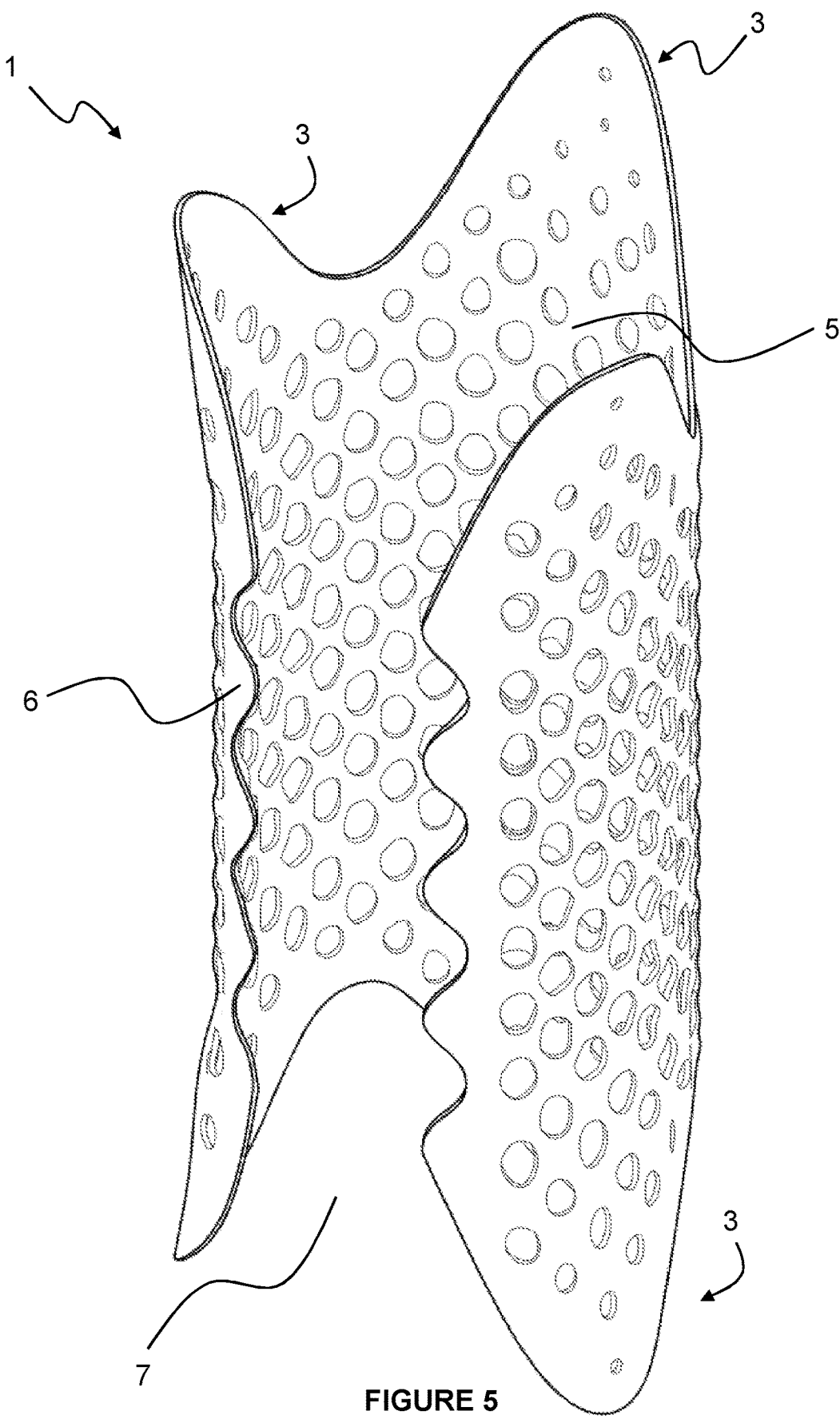
FIG. 5 is a perspective view of the device of FIGS. 1 to 4 in a deployed configuration.
Figure 6:
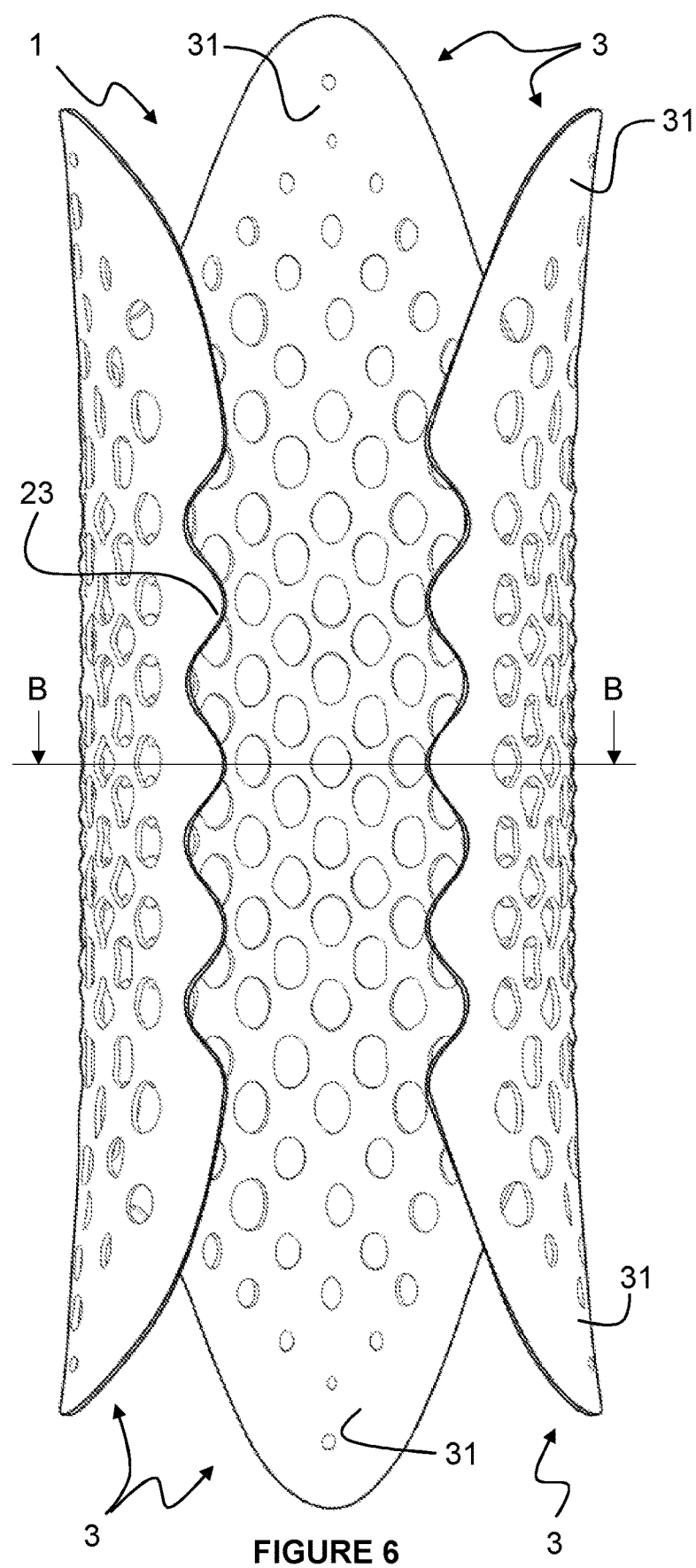
FIG. 6 is a front view of the device of FIGS. 1 to 5 in the deployed configuration.

Referring now to FIGS. 5 and 6 the stent 1 is shown in a flexed condition, with the anchoring portions 3 shown in a deployed configuration, which occurs by virtue of the inversion of the central portion 5. More particularly, the axial sides 32 are forced into having a positive curvature, which is illustrated most clearly in FIG. 9. In this, flexed condition the central part 31 and axial sides 32 together provide a curvature having a composite radius such that the anchoring portions 3 together provide a lobed shape, specifically a tri-lobed shape in this embodiment, when viewed from the end. The tip of each anchoring portion 3, corresponding to one of the lobes, projects outwardly with respect to the central portion 5 of the body 2. Other configurations are also envisaged, for example with more or less anchoring portions 3 extending from each end 2*a*, 2*b* of the body 2 and/or with the number of anchoring portions 3 extending from the first end 2*a* being different to the number of anchoring portions 3 extending from the second end 2*b*.

The axial edges 21, in this flexed state, are biased away from one another, tending to create an opening 7 therebetween. The opening 7 is preferable to ensure that there is space to maintain respiratory function through the trachea and stent 1 during surgery and also increase the airflow to the trachea. The opening bias causes the body 2 to bear against the wall of the lumen thereby providing compressive strength. It is envisaged that in certain applications the device is sized such that the axial edges 21 do not form a gap. It is also envisaged that in other applications the device is sized such that the axial edges 21 are in overlapping relation to one another.

Figure 7:
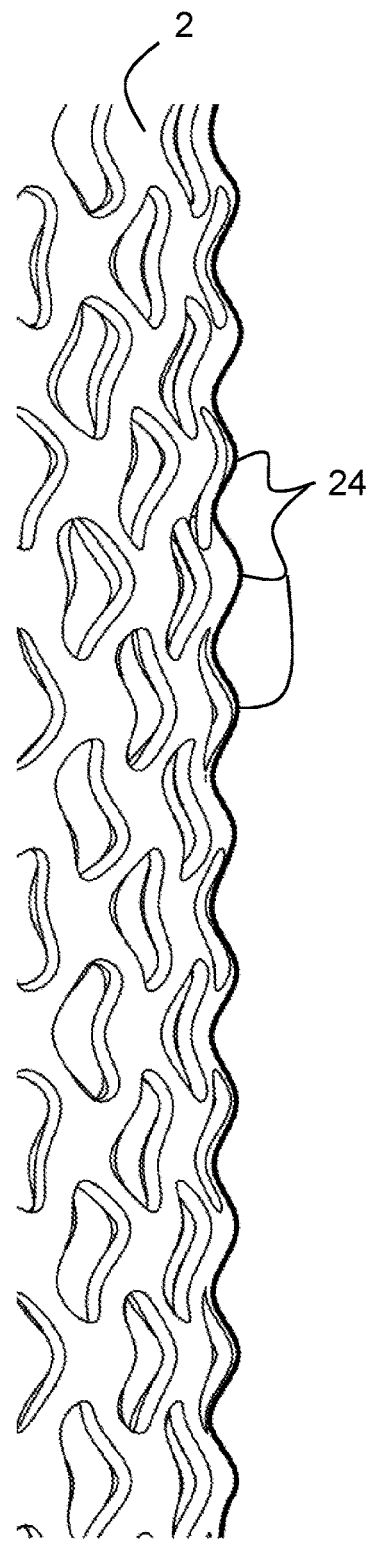
FIG. 7 is an enlarged view of a segment of the body of the device of FIGS. 1 to 6.
Figure 8:
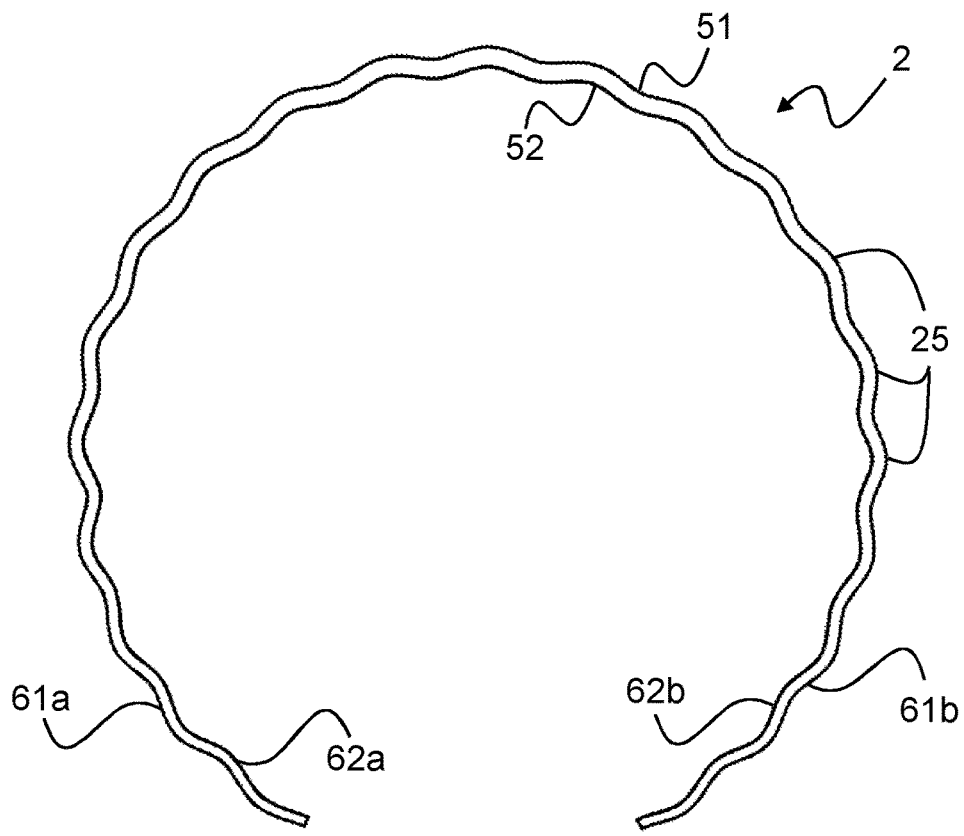
FIG. 8 is a section view through line B-B of FIG. 6.

FIG. 7 illustrates the circumferential undulations 24 of the body 2, while FIG. 8 illustrates the axial undulations 25. FIG. 8 also shows a cross sectional view of the stent 1 through the axis B-B of FIG. 6, illustrating that both the central portion 5 and edge portions 6 have positive curvature when the body 2 is in a flexed condition. When the body 2 is in a flexed condition the first major central surface 51 is generally convex while the second major central surface 52 is generally concave and the central portion 5 has a positive curvature.

The first major edge surfaces 61a, 61b remain generally convex while the second major edge surfaces 62a, 62b remain generally concave and the edge portions 6 maintain their positive curvature.

Figure 9:
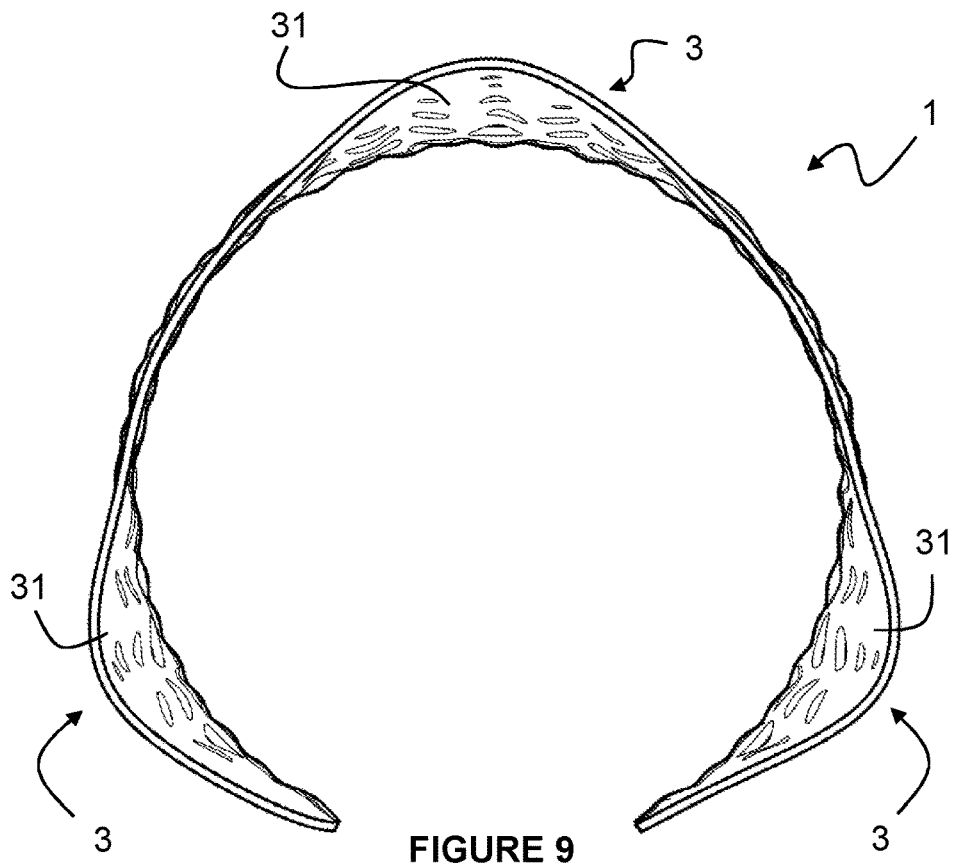
FIG. 9 is a top view of the device of FIGS. 1 to 8 in the deployed configuration.

As illustrated in FIG. 9, with the stent 1 in a flexed condition the central part 31 of each anchoring portion 3 is biased toward extending outwardly of the body 2. This causes the anchoring portions 3 to bear against the wall in the healthy area of the trachea, thereby to inhibit movement of the stent 1 once it has been deployed.

Figure 10:
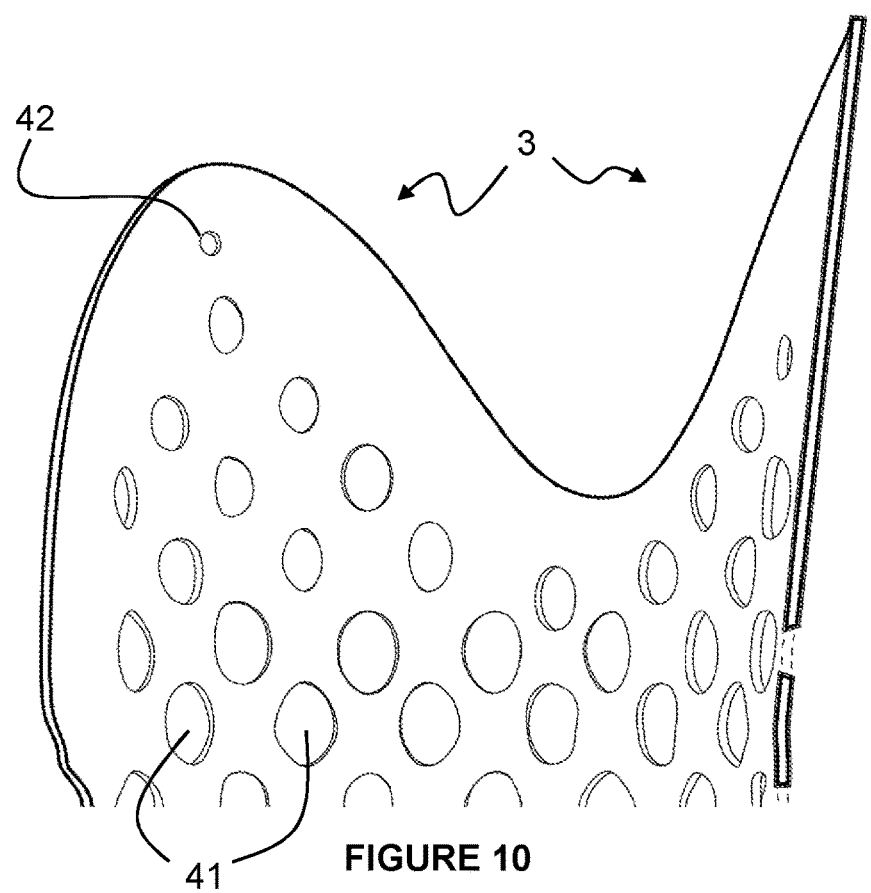
FIG. 10 is an enlarged part-sectional view of the device of FIGS. 1 to 9 through a central one of the anchoring portions.
Figure 11:
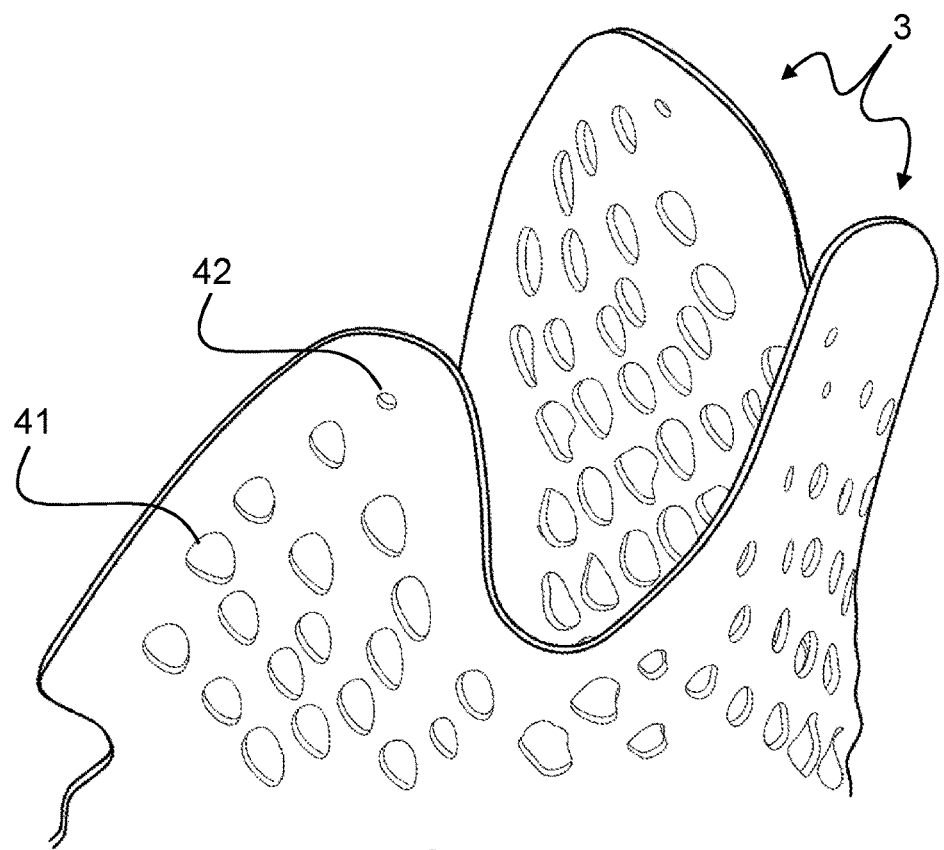
FIG. 11 is an enlarged perspective view of the anchoring portions of the device of FIGS. 1 to 10 in the relaxed condition.

Referring now to FIGS. 10 and 11, the anchoring portions 3 are shown with anchoring portion perforations 41 and retaining holes 42. The gentle outward slant of the centre of the anchor portions 3 in the flexed condition is also illustrated in FIG. 10, as compared with their gentle inward slant in the relaxed condition illustrated in FIG. 11. It is envisaged that the central portions 31 may be configured, additionally or alternatively, to converge in the relaxed condition such that when the central portion 5 of the body 2 is inverted, the anchoring portions 3 extend outwardly.

Figure 12:
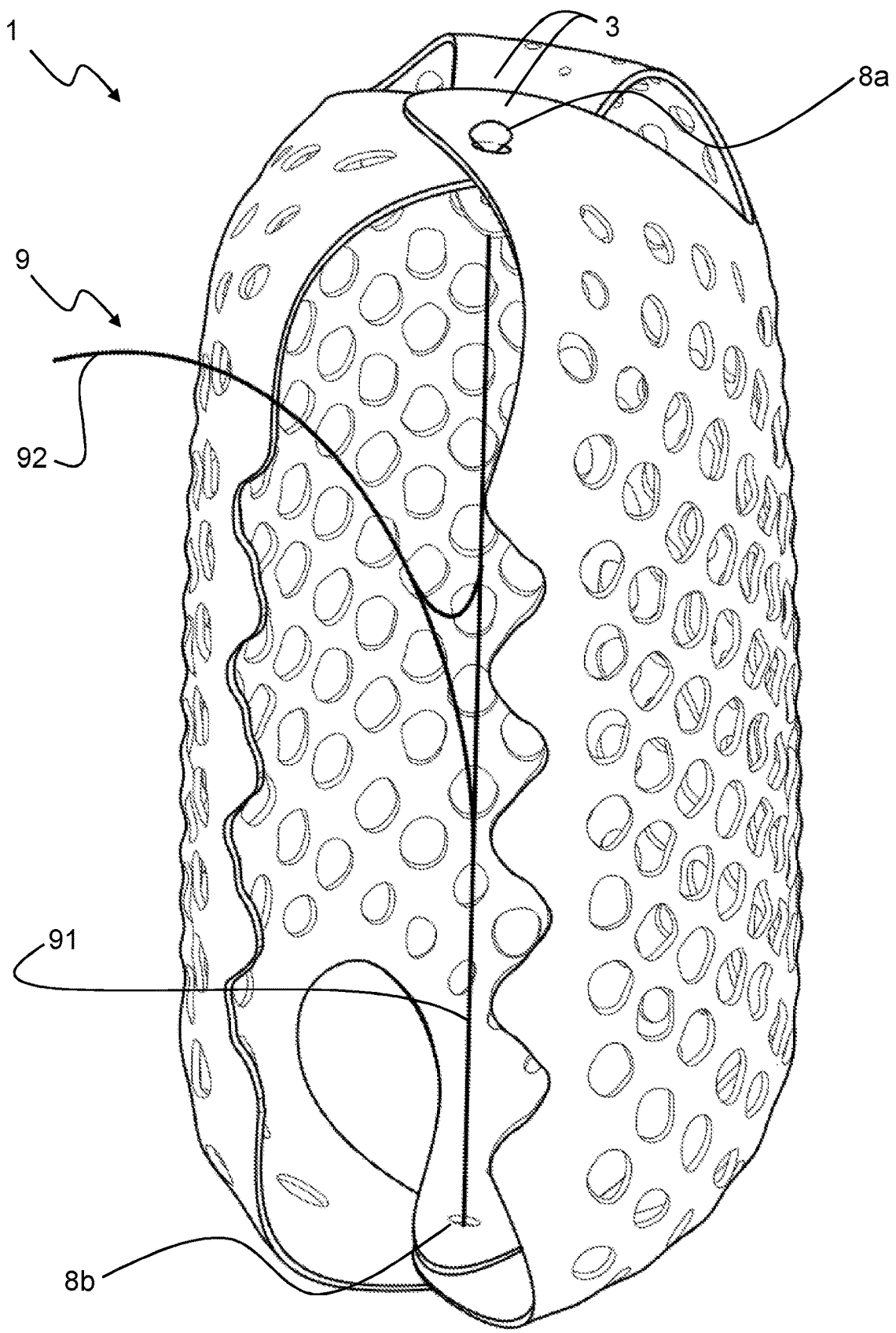
FIG. 12 is a perspective view of the device of FIGS. 1 to 11 shown in the loading configuration.

Referring now to FIG. 12, the stent 1 is shown in a loading configuration for allowing the insertion of the stent 1 into a lumen. To achieve the loading configuration, the stent 1 is inverted into its flexed condition, the six anchoring portions 3 are folded inwardly to an overlapping relationship and a retaining means 8a, 8b, 9 is attached to the outermost anchoring portion 3 via the retaining holes 42. The stent 1 is held in the loading configuration by aligning the retaining holes 42 on the anchoring portions 3 at each end of the stent 1 and passing the first section 91 of a release cord 9 through the retaining holes 42. The first section 91 extends between retaining members 8a, 8b located outside of the stent 1 at each of its ends. In this embodiment, the retaining members 8a, 8b are a pair of biodegradable stowing pins 8a, 8b connected orthogonal to the first section 91. The stowing pins 8a, 8b are sufficiently wide as to not slip back through the retention holes 42 hence preventing the inadvertent deployment of the stent 1.

The release cord 9 also has a second section 92 connected at one its ends to the first section 91 intermediate of the stowing pins 8a, 8b and at its second end provides a free end. The second section 92 passes from the first section 91 through the opening 7. The surgeon can apply a tensile force to the free end of the release cord 9 to deploy the stent 1. In this embodiment, the stowing pins 8a, 8b are of such a size as to be forced through the holes 42 and remain intact with the release cord 9. In some embodiments, however, the stowing pins 8a, 8b are frangibly connected to the release cord 9, such that they break away therefrom when the tensile force is applied. Release of the anchoring portions 3 results in anchoring portions 3 and the body 2 expanding such that the stent takes up a deployed configuration in which the body 2 and anchoring portion 3 bear, in use, against the wall of a lumen.

Figure 13:
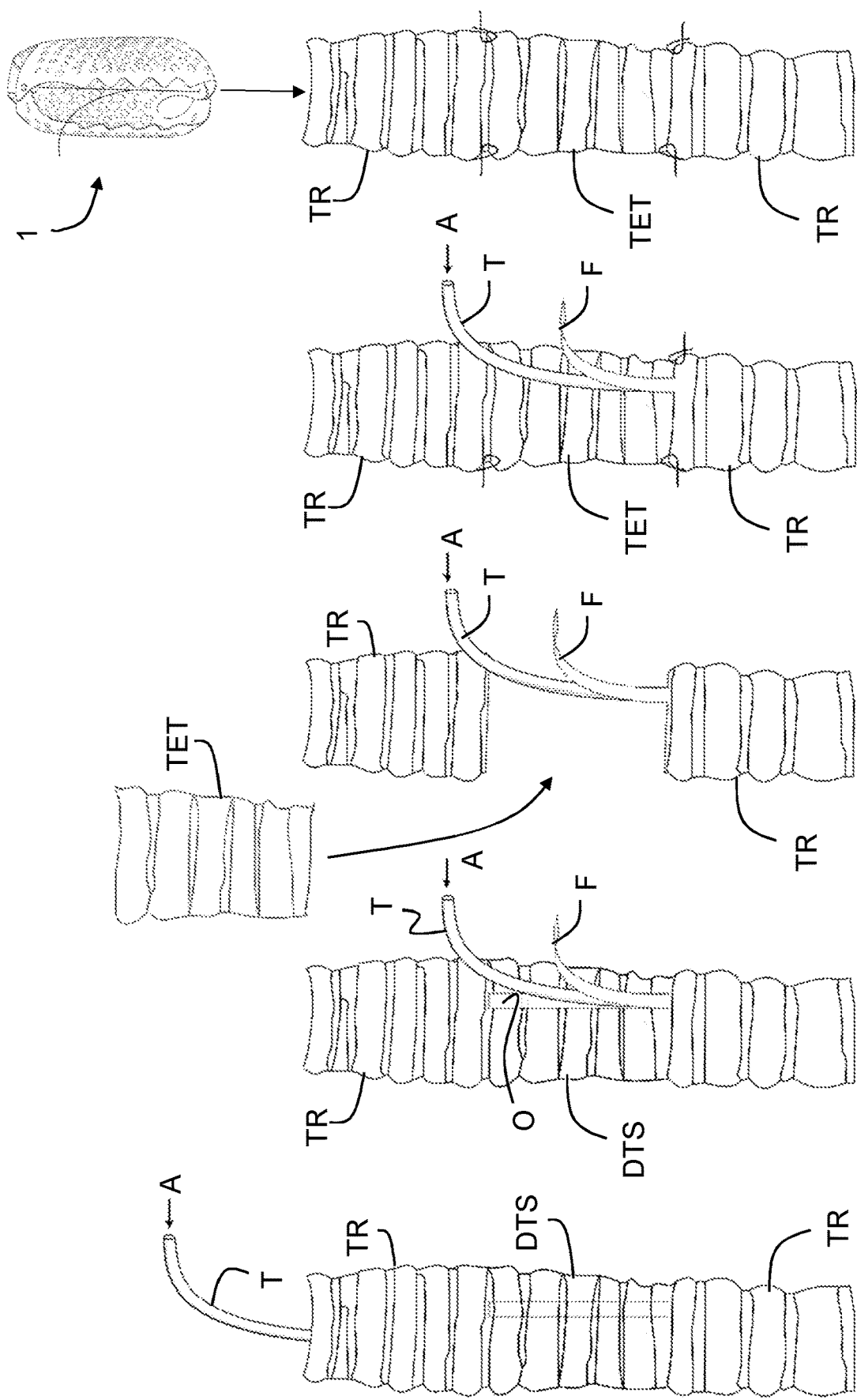
FIG. 13 is a schematic illustrating a first tracheal resection procedure using the device of FIGS. 1 to 12 in a loading configuration.
Figure 14:
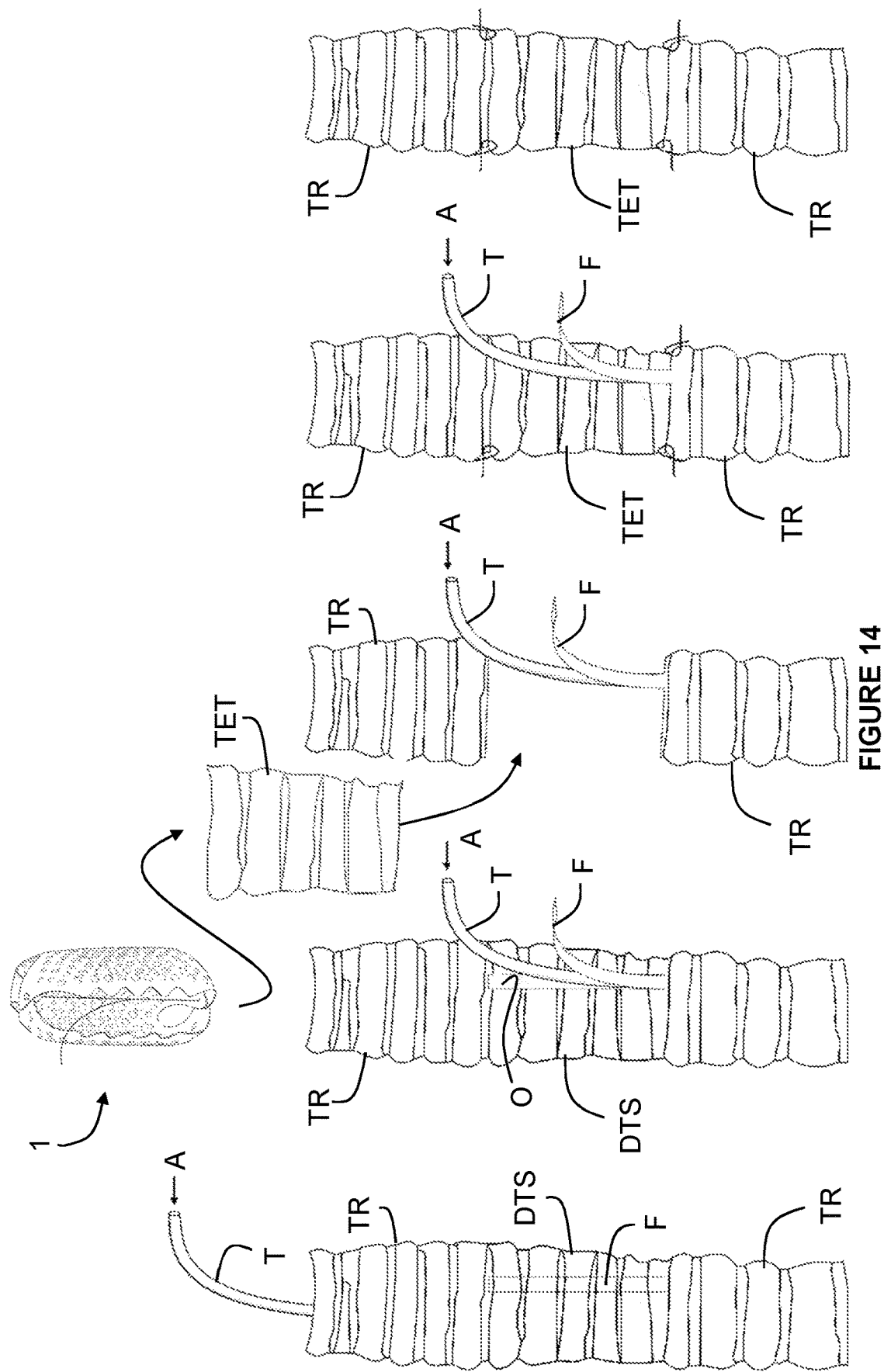
FIG. 14 is a schematic illustrating a second tracheal resection procedure using the device of FIGS. 1 to 12 in a loading configuration.

Referring now to FIGS. 13 and 14, there is shown a schematic representation of each of two trachea resection procedures. In both procedures, a tube T is inserted into the trachea TR of a patient and air A is introduced into the tube T. An elongate opening O is formed in the trachea TR along a defective trachea section DTS with a flap F being formed for grippage of the lower section of the trachea TR. The tube T is then drawn through the opening O or a further tube T is inserted therethrough through which air is introduced for the resection procedure. The defective trachea section DTS is then removed and a section of tissue engineered trachea TET is secured in its place, after which the flap F and tube T are removed to complete the resection procedure. The loading configuration can either be used for inserting the stent 1 through a patents' mouth after the defective trachea section DTS has been replaced, as shown in FIG. 13, or inserted into the tissue engineered trachea TET prior to the resection procedure, as shown in FIG. 14.

It will be appreciated that any of the aforementioned features may be sized/dimensioned and may be present in any combination such that the design can be tailored to each individual lumen.

For the avoidance of doubt, the tracheal stent 1 of the present embodiment includes several different states or configurations or conditions. The relaxed condition is shown in FIGS. 1 to 4. The flexed condition wherein the body 2 of the relaxed condition is inverted or folded back on itself as shown in FIGS. 5 to 9. The loading configuration, wherein the tracheal stent 1 is in a flexed condition but in which the anchoring portions 3 are folded inwardly into overlapping relationship, is shown in FIGS. 12 to 14. The deployed configuration is best illustrated by FIGS. 5 to 9, wherein the body 2 is inverted or folded back on itself and the anchoring portions 3 extend outwardly from the end of the body 2. The deployed and released condition (not shown) as assumed during the procedure shown in FIG. 14 wherein the tracheal stent 1 is inserted into the tissue engineered trachea (TET) with the anchoring portions 3 released.

Figure 15:
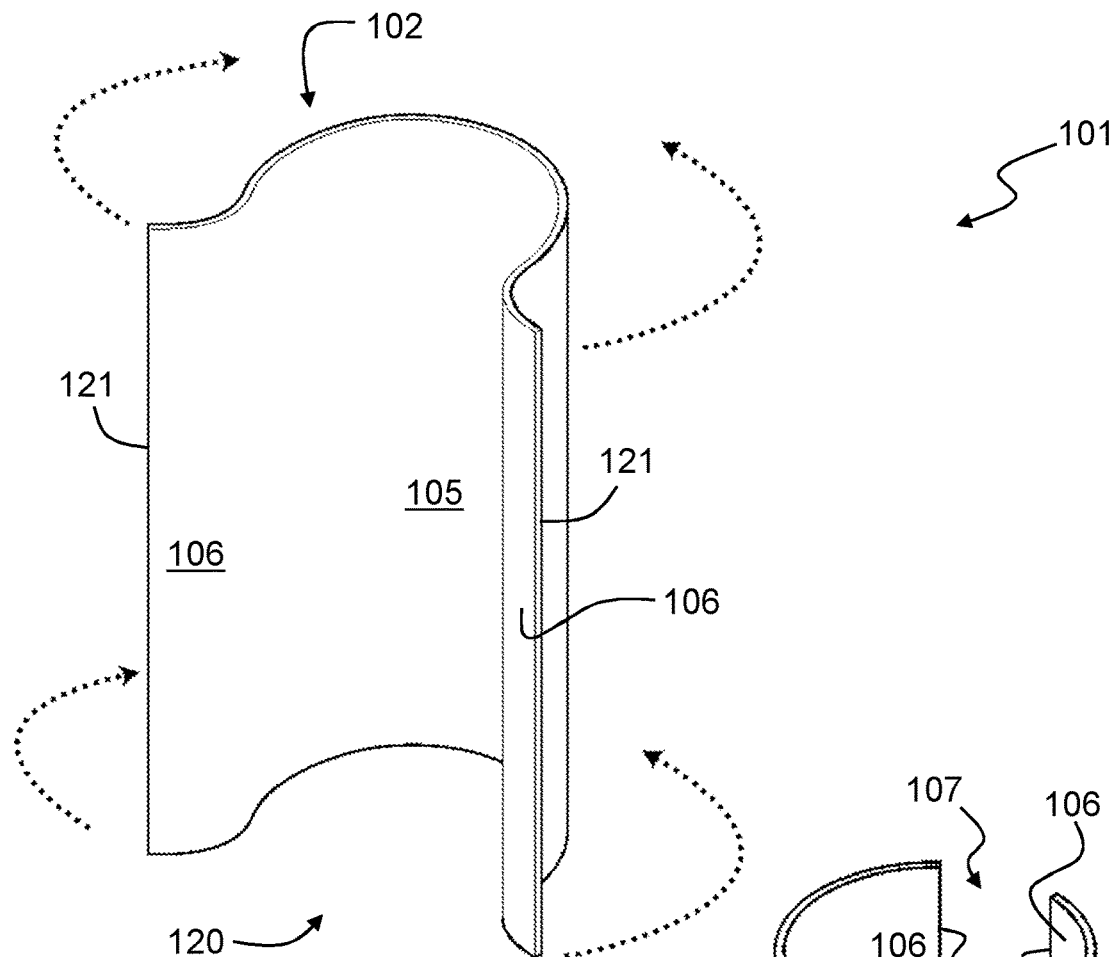
FIG. 15 is a perspective view of a self-expanding device according to another embodiment of the invention shown in a relaxed condition.
Figure 16:
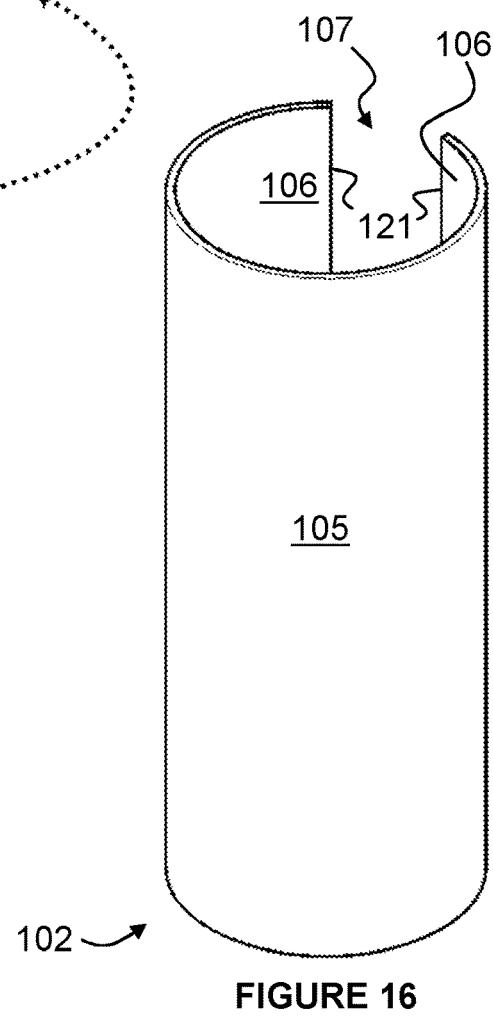
FIG. 16 is a perspective view of the device of FIG. 15 shown in a flexed condition.

Referring now to FIGS. 15 and 16, there is shown another embodiment of the invention similar to the embodiment above. The self-expanding device 101 of this embodiment differs from the stent 1 of the previous embodiment in that it is absent of any anchoring portions, edge features and surface features. More specifically, the device 101 includes a part-tubular body 102 having an open side 120 and a pair of axial edges 121. The body 102 has a central portion 105 and a pair of axial edge portions 106 joining the central portion 105 to the axial edges 121. As with the stent 1 described above, when the device 101 is in the relaxed condition, shown in FIG. 15, the central portion 105 has a negative curvature and the axial edge portions 106 have a positive curvature. When the device 101 is inverted to a flexed condition, shown in FIG. 16, the central portion 105 and the axial edge portions 106 all have a positive curvature and the central portion 105 is in a flexed state, whereby the axial edges 121 are biased away from one another, tending to create an opening 107 therebetween. The device 101 can be configured for use for any bodily intra-luminal support or indeed several non-medical applications, such as flexible tube connections or weakened wall sections in any tubular segments or cavities or for repair to any tubular structure and infrastructure where the outside of the structure is not accessible.

Figure 17:
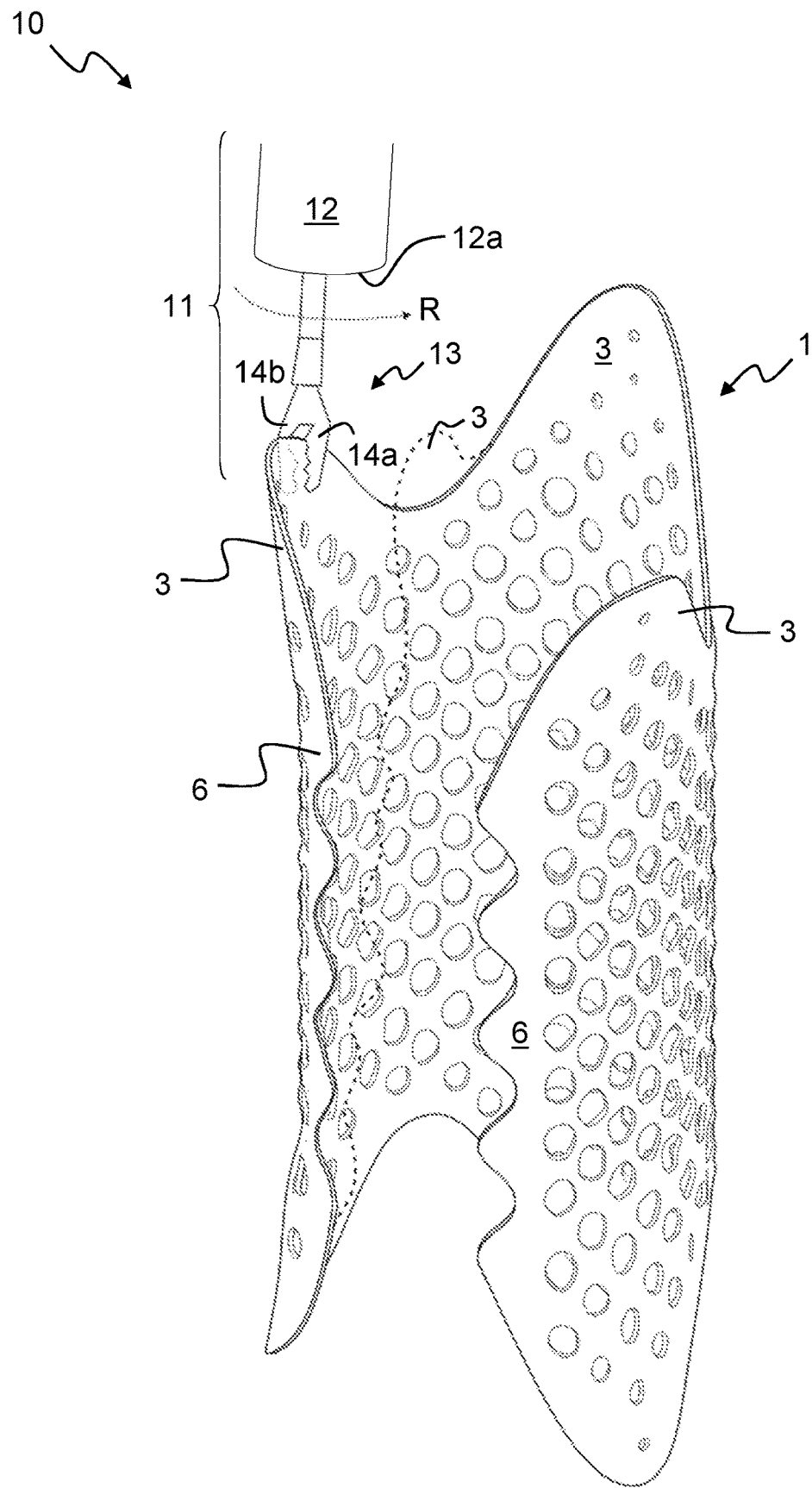
FIG. 17 is a perspective view of a surgical kit according to an embodiment of the invention showing how the self-expanding device of FIGS. 1 to 12 may be constricted for removal from a lumen.

Referring now to FIG. 17, there is shown a surgical kit 10 including a surgical tool 11 and the self-expanding device 1 of FIGS. 1 to 12, wherein like references depict like features that will not be discussed further herein. As shown in FIG. 17, the surgical tool 11 includes a tubular member 12 and a gripping tool 13 extending from a surgical end 12a of the tubular member 12. The gripping tool 13 has a pair of jaws 14a, 14b, which are pivotally connected together for clamping part of the self-expanding device 1. The jaws 14a, 14b are also rotatable within the tubular member 12 (as indicated by the dashed arrow R) and retractable into the tubular member 12.

In use, the gripping tool 13 is operated to close the jaws 14a, 14b to grab or grip the anchor portion 3 adjacent one of the axial edge portions 6. The gripping tool 13 is then operated to rotate the closed jaws 14a, 14b to coil or constrict self-expanding device 1 from its deployed configuration, thereby releasing it from the walls of the lumen (not shown) as illustrated by the dashed line. The gripping tool 13 is further operated to retract the jaws 14a, 14b and coiled or constricted self-expanding device 1 into the tubular member 12 to remove the self-expanding device 1 from the lumen (not shown).

It will be appreciated by those skilled in the art that several variations to the aforementioned embodiments are envisaged without departing from the scope of the invention. It will also be appreciated by those skilled in the art that any number of combinations of the aforementioned features and/or those shown in the appended drawings provide clear advantages over the prior art and are therefore within the scope of the invention described herein.

The invention claimed is:

1. A self-expandable stent comprising a flexible, part-tubular body having an open side with a pair of axial edges extending therealong, the body comprising a central portion and a pair of axial edge portions joining the central portion to the axial edges, at least part of the body being invertible from a relaxed, part-tubular condition to a flexed, inverted part-tubular condition in which the axial edges overlap or converge toward one another for insertion and release in a lumen to expand, bear against and support a wall of the lumen, each axial edge portion having a positive curvature both when the body is in the relaxed condition and when the body is in the flexed condition, the central portion having a negative curvature when the body is in the relaxed condition and a positive curvature when the body is in the flexed condition.

2. Stent according to claim 1, wherein the central portion of the body has a first thickness and each axial edge portion has a second thickness less than the first thickness.

3. Stent according to claim 1, wherein the axial edges are configured to avoid penetrating into or damaging the lumen when the body is inverted and released therein.

4. Stent according to claim 3, wherein the axial edges undulate to provide a series of curved projections for engaging the lumen wall without penetration therein.

5. Stent according to claim 1 comprising one or more anchoring portions extending axially from an end of the body when the body is in the relaxed condition, wherein the or each anchoring portion is configured such that when the body or body portion is inverted to the flexed condition the or each anchoring portion is biased toward extending axially and outwardly from the end of the body, thereby to bear against the wall of the lumen for inhibiting movement of the stent and reducing the pressure exerted, in use, on the lumen wall by the axial edge portions.

6. Stent according to claim 5 comprising one or more anchoring portions extending axially from another end of the body when the body is in the relaxed condition, wherein each anchoring portion is configured such that when the body or body portion is inverted to the flexed condition each anchoring portion is biased toward extending outwardly from the end of the body, thereby to bear against the wall of the lumen for inhibiting movement of the stent.

7. Stent according to claim 5, wherein the or each anchoring portion extends axially inwardly from the end of the body when the body is in the relaxed condition.

8. Stent according to claim 5, wherein the or each anchoring portion includes a positive curvature when the body is in both the relaxed and flexed conditions.

9. Stent according to claim 8, wherein the or each anchoring portion includes a central part having a positive curvature and axial sides each having a negative curvature when the body is in the relaxed condition.

10. Stent according to claim 5, wherein the one or more anchoring portions comprise two or more anchoring portions extending from each end which diverge from one another when the body is in the flexed condition.

11. A self-expandable stent comprising a flexible, part-tubular body having an open side with a pair of axial edges extending therealong, the body comprising a central portion and a pair of axial edge portions joining the central portion to the axial edges, at least part of the body being invertible from a relaxed, part-tubular condition to a flexed, inverted part-tubular condition in which the axial edges overlap or converge toward one another for insertion and release in a lumen to expand, bear against and support a wall of the lumen, wherein the or a central portion of the body has a first thickness and the or a pair of axial edge portions joining the central portion to the axial edges of the body each have a second thickness less than the first thickness.

12. Stent according to claim 11, wherein the axial edges undulate to provide a series of curved projections for engaging the lumen wall without penetration therein.

13. A self-expandable stent comprising a flexible, part-tubular body having an open side with a pair of axial edges extending therealong and one or more anchoring portions extending axially from at least one end thereof, at least part of the body being invertible from a relaxed, part-tubular condition to a flexed, inverted part-tubular condition in which the axial edges overlap or converge toward one another, wherein the or each anchoring portion is configured such that when the body or body portion is inverted to the flexed condition the or each anchoring portion is biased toward extending axially and outwardly from the end of the body, thereby to bear against the wall of the lumen for inhibiting movement of the stent.

14. Stent according to claim 13 comprising one or more anchoring portions extending axially from another end of the body when the body is in the relaxed condition, wherein each anchoring portion is configured such that when the body or body portion is inverted to the flexed condition each anchoring portion is biased toward extending outwardly from the end of the body, thereby to bear against the wall of the lumen for inhibiting movement of the stent.

15. Stent according to claim 13, wherein each anchoring portion extends axially inwardly from the end of the body when the body is in the relaxed condition.

16. Stent according to claim 13, wherein the or each anchoring portion includes a positive curvature when the body is in both the relaxed and flexed conditions.

17. Stent according to claim 16, wherein the or each anchoring portion includes a central part having a positive curvature and axial sides each having a negative curvature when the body is in the relaxed condition.

18. Stent according to claim 13, wherein the one or more anchoring portions comprise two or more anchoring portions extending from each end which diverge from one another when the body is in the flexed condition.

19. Stent according to claim 18 comprising a loading configuration in which the anchoring portions extending from each end can be folded inwardly and held in an overlapping relationship to retain the body in its flexed condition for insertion in the lumen.

20. Stent according to claim 19, wherein each anchoring portion includes a retaining hole through its thickness and adjacent a free end thereof, the stent comprising a release cord extending through the hole and a stowing pin engaging each anchoring portion to hold the anchoring portions and retaining the body in the flexed condition for insertion in the lumen.

\* \* \* \* \*